United States Patent
Schuh et al.

(10) Patent No.: US 11,638,618 B2
(45) Date of Patent: May 2, 2023

(54) SYSTEMS AND METHODS FOR ALIGNING INPUTS ON MEDICAL INSTRUMENTS

(71) Applicant: Auris Health, Inc., Redwood City, CA (US)

(72) Inventors: Travis Michael Schuh, Los Altos, CA (US); David Stephen Mintz, Los Altos Hills, CA (US)

(73) Assignee: Auris Health, Inc., Redwood City, CA (US)

( * ) Notice: Subject to any disclaimer, the term of this patent is extended or adjusted under 35 U.S.C. 154(b) by 221 days.

(21) Appl. No.: 16/797,588

(22) Filed: Feb. 21, 2020

(65) Prior Publication Data
US 2020/0297437 A1  Sep. 24, 2020

Related U.S. Application Data

(60) Provisional application No. 62/822,676, filed on Mar. 22, 2019.

(51) Int. Cl.
*A61B 34/00* (2016.01)
*A61G 13/08* (2006.01)
(Continued)

(52) U.S. Cl.
CPC .............. *A61B 34/30* (2016.02); *A61B 34/71* (2016.02); *A61B 90/98* (2016.02); *A61G 13/08* (2013.01);
(Continued)

(58) Field of Classification Search
CPC combination set(s) only.
See application file for complete search history.

(56) References Cited

U.S. PATENT DOCUMENTS

| 2,556,601 A | 6/1951 | Schofield |
| 2,566,183 A | 8/1951 | Forss |

(Continued)

FOREIGN PATENT DOCUMENTS

| CN | 103037799 | 4/2011 |
| CN | 102316817 | 1/2012 |

(Continued)

OTHER PUBLICATIONS

International search report and written opinion dated May 20, 2020 in application No. PCT/US20/19197.
(Continued)

*Primary Examiner* — Scott Luan
(74) *Attorney, Agent, or Firm* — Morgan, Lewis & Bockius LLP

(57) ABSTRACT

Certain aspects relate to systems and techniques for aligning inputs on medical instruments. In one aspect, the method includes receiving, at a data reader of the instrument drive mechanism, alignment data from the tool when the tool is positioned within a threshold distance of the data reader. The tool include one or more inputs and one or more pull wires configured to be actuated by output shafts of the instrument drive mechanism via the one or more inputs. The method also includes receiving, at a processor, the alignment data from the data reader, and rotating, via the processor, the one or more output shafts of the instrument drive mechanism into alignment with the one or more inputs of the tool based on the alignment data. Each of the output shafts is configured to mechanically couple with a corresponding one of the inputs of the tool.

29 Claims, 32 Drawing Sheets

(51) Int. Cl.
   *A61B 34/30* (2016.01)
   *A61G 13/10* (2006.01)
   *A61B 90/98* (2016.01)
   *A61B 17/00* (2006.01)

(52) U.S. Cl.
   CPC .. *A61G 13/101* (2013.01); *A61B 2017/00221* (2013.01); *A61B 2034/301* (2016.02); *A61B 2034/302* (2016.02); *A61B 2034/303* (2016.02)

(56) References Cited

U.S. PATENT DOCUMENTS

| | | | |
|---|---|---|---|
| 2,623,175 A | 12/1952 | Finke |
| 2,730,699 A | 1/1956 | Gratian |
| 2,884,808 A | 5/1959 | Mueller |
| 3,294,183 A | 12/1966 | Riley et al. |
| 3,472,083 A | 10/1969 | Schnepel |
| 3,513,724 A | 5/1970 | Box |
| 3,595,074 A | 7/1971 | Johnson |
| 3,734,207 A | 5/1973 | Fishbein |
| 3,739,923 A | 6/1973 | Totsuka |
| 3,784,031 A | 1/1974 | Nitu |
| 3,790,002 A | 2/1974 | Guilbaud et al. |
| 3,921,536 A | 11/1975 | Savage |
| 3,926,386 A | 12/1975 | Stahmann |
| 4,141,245 A | 2/1979 | Brandstetter |
| 4,241,884 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,507,026 A | 3/1985 | Lund |
| 4,530,471 A | 7/1985 | Inoue |
| 4,555,960 A | 12/1985 | King |
| 4,688,555 A | 8/1987 | Wardle |
| 4,745,908 A | 5/1988 | Wardle |
| 4,784,150 A | 11/1988 | Voorhies et al. |
| 4,857,058 A | 8/1989 | Payton |
| 4,907,168 A | 3/1990 | Boggs |
| 4,945,790 A | 8/1990 | Golden |
| 5,207,128 A | 5/1993 | Albright |
| 5,234,428 A | 8/1993 | Kaufman |
| 5,256,150 A | 10/1993 | Quiachon et al. |
| 5,277,085 A | 1/1994 | Tanimura et al. |
| 5,350,101 A | 9/1994 | Godlewski |
| 5,426,687 A | 6/1995 | Goodall et al. |
| 5,507,725 A | 4/1996 | Savage |
| 5,524,180 A | 6/1996 | Wang et al. |
| 5,559,294 A | 9/1996 | Hoium et al. |
| 5,709,661 A | 1/1998 | Van Egmond |
| 5,767,840 A | 6/1998 | Selker |
| 5,779,623 A | 7/1998 | Bonnell |
| 5,792,135 A | 8/1998 | Madhani et al. |
| 5,797,900 A | 8/1998 | Madhani |
| 5,855,583 A | 1/1999 | Wang et al. |
| 5,921,968 A | 7/1999 | Lampropoulos et al. |
| 5,967,934 A | 10/1999 | Ishida et al. |
| 6,077,219 A | 6/2000 | Viebach |
| 6,084,371 A | 7/2000 | Kress et al. |
| 6,154,000 A | 11/2000 | Rastegar et al. |
| 6,171,234 B1 | 1/2001 | White et al. |
| 6,185,478 B1 | 2/2001 | Koakutsu |
| 6,272,371 B1 | 8/2001 | Shlomo |
| 6,289,579 B1 | 9/2001 | Viza et al. |
| 6,394,998 B1 | 5/2002 | Wallace et al. |
| 6,401,572 B1 | 6/2002 | Provost |
| 6,436,107 B1 | 8/2002 | Wang et al. |
| 6,487,940 B2 | 12/2002 | Hart et al. |
| 6,491,701 B2 | 12/2002 | Tierney et al. |
| 6,695,818 B2 | 2/2004 | Wollschlager |
| 6,726,675 B1 | 4/2004 | Beyar |
| 6,786,896 B1 | 9/2004 | Madhani et al. |
| 6,827,712 B2 | 12/2004 | Tovey et al. |
| 7,044,936 B2 | 5/2006 | Harding |
| 7,172,580 B2 | 2/2007 | Hruska et al. |
| 7,276,044 B2 | 10/2007 | Ferry et al. |
| 7,615,042 B2 | 11/2009 | Beyar et al. |
| 7,635,342 B2 | 12/2009 | Ferry et al. |
| 7,766,856 B2 | 8/2010 | Ferry et al. |
| 7,938,809 B2 | 5/2011 | Lampropoulos et al. |
| 7,974,674 B2 | 7/2011 | Hauck et al. |
| 7,998,020 B2 | 8/2011 | Kidd et al. |
| 8,052,636 B2 | 11/2011 | Moll et al. |
| 8,157,308 B2 | 4/2012 | Pedersen |
| 8,182,415 B2 | 5/2012 | Larkin et al. |
| 8,277,417 B2 | 10/2012 | Fedinec et al. |
| 8,291,791 B2 | 10/2012 | Light et al. |
| 8,414,505 B1 | 4/2013 | Weitzner |
| 8,425,465 B2 | 4/2013 | Nagano |
| 8,671,817 B1 | 3/2014 | Bogusky |
| 8,720,448 B2 | 5/2014 | Reis et al. |
| 8,746,252 B2 | 6/2014 | McGrogan et al. |
| 8,870,815 B2 | 10/2014 | Bhat et al. |
| 8,961,533 B2 | 2/2015 | Stahler et al. |
| 8,968,333 B2 | 3/2015 | Yu et al. |
| 8,992,542 B2 | 3/2015 | Hagag et al. |
| 9,173,713 B2 | 11/2015 | Hart et al. |
| 9,204,933 B2 | 12/2015 | Reis et al. |
| 9,326,822 B2 | 5/2016 | Lewis et al. |
| 9,408,669 B2 | 8/2016 | Kokish et al. |
| 9,446,177 B2 | 9/2016 | Millman et al. |
| 9,452,018 B2 | 9/2016 | Yu |
| 9,457,168 B2 | 10/2016 | Moll et al. |
| 9,498,601 B2 | 11/2016 | Tanner et al. |
| 9,504,604 B2 | 11/2016 | Alvarez |
| 9,561,083 B2 | 2/2017 | Yu et al. |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 10,016,900 B1 | 7/2018 | Meyer et al. |
| 10,022,192 B1 | 7/2018 | Ummalaneni |
| 10,046,140 B2 | 8/2018 | Kokish et al. |
| 10,080,576 B2 | 9/2018 | Romo et al. |
| 10,136,959 B2 | 11/2018 | Mintz et al. |
| 10,143,360 B2 | 12/2018 | Roelle et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,213,264 B2 | 2/2019 | Tanner et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,383,765 B2 | 8/2019 | Alvarez et al. |
| 10,398,518 B2 | 9/2019 | Yu et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,454,347 B2 | 10/2019 | Covington et al. |
| 10,464,209 B2 | 11/2019 | Ho et al. |

(56) References Cited

U.S. PATENT DOCUMENTS

| | | |
|---|---|---|
| 10,470,830 B2 | 11/2019 | Hill |
| 10,478,595 B2 | 11/2019 | Kokish |
| 10,482,599 B2 | 11/2019 | Mintz et al. |
| 10,493,239 B2 | 12/2019 | Hart et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,524,867 B2 | 1/2020 | Kokish et al. |
| 10,539,478 B2 | 1/2020 | Lin |
| 10,543,048 B2 | 1/2020 | Noonan et al. |
| 10,555,778 B2 | 2/2020 | Ummalaneni et al. |
| 10,556,092 B2 | 2/2020 | Yu et al. |
| 10,569,052 B2 | 2/2020 | Kokish et al. |
| 2001/0042643 A1 | 11/2001 | Krueger et al. |
| 2002/0045905 A1 | 4/2002 | Gerbi et al. |
| 2002/0098938 A1 | 7/2002 | Milbourne et al. |
| 2002/0100254 A1 | 8/2002 | Dharssi |
| 2002/0107573 A1 | 8/2002 | Steinberg |
| 2002/0117017 A1 | 8/2002 | Bernhardt et al. |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0056561 A1 | 3/2003 | Butscher et al. |
| 2003/0212308 A1 | 11/2003 | Bendall |
| 2004/0015053 A1 | 1/2004 | Bieger |
| 2004/0152972 A1 | 8/2004 | Hunter |
| 2004/0243147 A1 | 12/2004 | Lipow |
| 2004/0254566 A1 | 12/2004 | Plicchi |
| 2005/0004579 A1 | 1/2005 | Schneider et al. |
| 2005/0177026 A1 | 8/2005 | Hoeg et al. |
| 2005/0183532 A1 | 8/2005 | Najaf et al. |
| 2005/0222554 A1 | 10/2005 | Wallace et al. |
| 2006/0041245 A1 | 2/2006 | Ferry |
| 2006/0111692 A1 | 5/2006 | Hlavka et al. |
| 2006/0146010 A1 | 7/2006 | Schneider |
| 2006/0201688 A1 | 9/2006 | Jenner et al. |
| 2006/0229587 A1 | 10/2006 | Beyar et al. |
| 2006/0237205 A1 | 10/2006 | Sia et al. |
| 2007/0000498 A1 | 1/2007 | Glynn et al. |
| 2007/0013336 A1 | 1/2007 | Nowlin et al. |
| 2007/0060879 A1 | 3/2007 | Weitzner et al. |
| 2007/0100201 A1 | 5/2007 | Komiya et al. |
| 2007/0100254 A1 | 5/2007 | Murakami |
| 2007/0112355 A1 | 5/2007 | Salahieh |
| 2007/0119274 A1 | 5/2007 | Devengenzo et al. |
| 2007/0149946 A1 | 6/2007 | Viswanathan |
| 2007/0191177 A1 | 8/2007 | Nagai et al. |
| 2007/0239028 A1 | 10/2007 | Houser |
| 2007/0245175 A1 | 10/2007 | Zheng et al. |
| 2007/0299427 A1 | 12/2007 | Yeung et al. |
| 2008/0039255 A1 | 2/2008 | Jinno et al. |
| 2008/0046122 A1 | 2/2008 | Manzo et al. |
| 2008/0065103 A1 | 3/2008 | Cooper et al. |
| 2008/0147011 A1 | 6/2008 | Urmey |
| 2008/0177285 A1 | 7/2008 | Brock et al. |
| 2008/0214925 A1 | 9/2008 | Wilson et al. |
| 2008/0243064 A1 | 10/2008 | Stahler et al. |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0287963 A1 | 11/2008 | Rogers |
| 2008/0302200 A1 | 12/2008 | Tobey |
| 2009/0082722 A1 | 3/2009 | Munger et al. |
| 2009/0098971 A1 | 4/2009 | Ho et al. |
| 2009/0105645 A1 | 4/2009 | Kidd et al. |
| 2009/0163948 A1 | 6/2009 | Sunaoshi |
| 2009/0171371 A1 | 7/2009 | Nixon |
| 2009/0247944 A1 | 10/2009 | Kirschenman et al. |
| 2009/0248039 A1 | 10/2009 | Cooper et al. |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0130923 A1 | 5/2010 | Cleary et al. |
| 2010/0130987 A1 | 5/2010 | Wenderow et al. |
| 2010/0170519 A1* | 7/2010 | Romo ............... A61B 34/30 128/852 |
| 2010/0175701 A1 | 7/2010 | Reis et al. |
| 2010/0204646 A1 | 8/2010 | Plicchi et al. |
| 2010/0210923 A1 | 8/2010 | Li et al. |
| 2010/0248177 A1 | 9/2010 | Mangelberger et al. |
| 2010/0249506 A1 | 9/2010 | Prisco et al. |
| 2010/0274078 A1 | 10/2010 | Kim et al. |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0028991 A1 | 2/2011 | Ikeda et al. |
| 2011/0130718 A1 | 6/2011 | Kidd et al. |
| 2011/0147030 A1 | 6/2011 | Blum et al. |
| 2011/0152880 A1 | 6/2011 | Alvarez et al. |
| 2011/0238083 A1 | 9/2011 | Moll et al. |
| 2011/0261183 A1 | 10/2011 | Ma et al. |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0232476 A1 | 9/2012 | Bhat et al. |
| 2012/0239012 A1 | 9/2012 | Laurent et al. |
| 2012/0277730 A1 | 11/2012 | Salahieh |
| 2012/0283747 A1 | 11/2012 | Popovic |
| 2013/0018400 A1 | 1/2013 | Milton et al. |
| 2013/0144116 A1 | 6/2013 | Cooper et al. |
| 2013/0231678 A1 | 9/2013 | Wenderow |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0066944 A1 | 3/2014 | Taylor et al. |
| 2014/0069437 A1 | 3/2014 | Reis et al. |
| 2014/0142591 A1 | 5/2014 | Alvarez et al. |
| 2014/0166023 A1 | 6/2014 | Kishi |
| 2014/0171778 A1 | 6/2014 | Tsusaka |
| 2014/0180063 A1 | 6/2014 | Zhao |
| 2014/0222019 A1 | 8/2014 | Brudnick |
| 2014/0243849 A1 | 8/2014 | Saglam et al. |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276935 A1 | 9/2014 | Yu |
| 2014/0276936 A1 | 9/2014 | Kokish et al. |
| 2014/0277334 A1 | 9/2014 | Yu et al. |
| 2014/0357984 A1 | 12/2014 | Wallace et al. |
| 2014/0364870 A1 | 12/2014 | Alvarez et al. |
| 2014/0375784 A1 | 12/2014 | Massetti |
| 2015/0012134 A1 | 1/2015 | Robinson |
| 2015/0090063 A1 | 4/2015 | Lantermann et al. |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |
| 2015/0150635 A1 | 6/2015 | Kilroy |
| 2015/0182250 A1 | 7/2015 | Conlon et al. |
| 2015/0231364 A1 | 8/2015 | Blanchard |
| 2015/0374445 A1 | 12/2015 | Gombert et al. |
| 2016/0000512 A1 | 1/2016 | Gombert et al. |
| 2016/0001038 A1 | 1/2016 | Romo et al. |
| 2016/0157945 A1 | 6/2016 | Madhani |
| 2016/0166234 A1 | 6/2016 | Zhang |
| 2016/0192860 A1 | 7/2016 | Allenby |
| 2016/0206389 A1 | 7/2016 | Miller |
| 2016/0213435 A1 | 7/2016 | Hourtash |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0338783 A1 | 11/2016 | Romo et al. |
| 2016/0338785 A1 | 11/2016 | Kokish et al. |
| 2016/0346049 A1 | 12/2016 | Allen et al. |

(56) References Cited

U.S. PATENT DOCUMENTS

| | | |
|---|---|---|
| 2017/0007337 A1 | 1/2017 | Dan |
| 2017/0007343 A1 | 1/2017 | Yu |
| 2017/0119481 A1 | 5/2017 | Romo et al. |
| 2017/0151028 A1 | 6/2017 | Ogawa et al. |
| 2017/0165011 A1 | 6/2017 | Bovay et al. |
| 2017/0202627 A1 | 7/2017 | Sramek et al. |
| 2017/0209073 A1 | 7/2017 | Sramek et al. |
| 2017/0252540 A1 | 9/2017 | Weitzner et al. |
| 2017/0258534 A1 | 9/2017 | Hourtash |
| 2017/0281049 A1 | 10/2017 | Yamamoto |
| 2017/0290631 A1 | 10/2017 | Lee et al. |
| 2017/0340396 A1 | 11/2017 | Romo et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0049792 A1 | 2/2018 | Eckert |
| 2018/0056044 A1 | 3/2018 | Choi et al. |
| 2018/0104820 A1 | 4/2018 | Troy et al. |
| 2018/0116735 A1 | 5/2018 | Tierney et al. |
| 2018/0206927 A1 | 7/2018 | Prisco et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0221101 A1 | 8/2018 | Prisco et al. |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0296299 A1 | 10/2018 | Iceman |
| 2018/0303566 A1 | 10/2018 | Soundararajan |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0110839 A1 | 4/2019 | Rafii-Tari et al. |
| 2019/0151148 A1 | 4/2019 | Alvarez et al. |
| 2019/0142537 A1 | 5/2019 | Covington et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0228525 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |
| 2020/0039086 A1 | 2/2020 | Meyer |
| 2020/0046434 A1 | 2/2020 | Graetzel |
| 2020/0054405 A1 | 2/2020 | Schuh |
| 2020/0054408 A1 | 2/2020 | Schuh et al. |
| 2020/0060516 A1 | 2/2020 | Baez |
| 2020/0086087 A1 | 3/2020 | Hart et al. |
| 2020/0091799 A1 | 3/2020 | Covington et al. |
| 2020/0093549 A1 | 3/2020 | Chin |
| 2020/0093554 A1 | 3/2020 | Schuh |
| 2020/0100845 A1 | 4/2020 | Julian |
| 2020/0100853 A1 | 4/2020 | Ho |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0129252 A1 | 4/2020 | Kokish |
| 2020/0146769 A1 | 5/2020 | Eyre |
| 2020/0155245 A1 | 5/2020 | Yu |
| 2020/0155801 A1 | 5/2020 | Kokish |

FOREIGN PATENT DOCUMENTS

| | | |
|---|---|---|
| CN | 102458295 | 5/2012 |
| CN | 102665590 | 9/2012 |
| CN | 102973317 | 3/2013 |
| CN | 102015759 | 4/2013 |
| CN | 103735313 | 4/2014 |
| CN | 105559850 | 5/2016 |
| CN | 105559886 | 5/2016 |
| DE | 19649082 | 1/1998 |
| DE | 102004020465 | 9/2005 |
| EP | 1 442 720 | 8/2004 |
| EP | 2 567 670 | 3/2013 |
| EP | 3 025 630 | 6/2016 |
| JP | 07-136173 | 5/1995 |
| JP | 2009-139187 | 6/2009 |
| JP | 2010-046384 | 3/2010 |
| WO | WO 02/74178 | 9/2002 |
| WO | WO 07/146987 | 12/2007 |
| WO | WO 09/092059 | 7/2009 |
| WO | WO 11/005335 | 1/2011 |
| WO | WO 12/037506 | 3/2012 |
| WO | WO 13/179600 | 12/2013 |
| WO | WO-2014/020571 A1 | 2/2014 |
| WO | WO 15/127231 | 8/2015 |
| WO | WO-2016/044574 A1 | 3/2016 |
| WO | WO 17/059412 | 4/2017 |
| WO | WO 17/151993 | 9/2017 |
| WO | WO-2019/143458 A1 | 7/2019 |
| WO | WO-2021/024090 A1 | 2/2021 |

OTHER PUBLICATIONS

Mayo Clinic, Robotic Surgery, https://www.mayoclinic.org/tests-procedures/robotic-surgery/about/pac-20394974?p=1, downloaded from the internet on Jul. 12, 2018, 2 pp.

Extended European Search Report for Application No. 20776819.3, dated Sep. 20, 2022, 11 pages.

* cited by examiner

SYSTEMS AND METHODS FOR ALIGNING INPUTS ON MEDICAL INSTRUMENTS

CROSS-REFERENCE TO RELATED APPLICATION(S)

This application claims the benefit of U.S. Provisional Application No. 62/822,676, filed Mar. 22, 2019, which is hereby incorporated by reference in its entirety.

TECHNICAL FIELD

The systems and methods disclosed herein are directed to aligning inputs of medical instruments and more particularly to aligning the inputs of a medical tool with corresponding output shafts of an instrument drive mechanism.

BACKGROUND

During a medical procedure, a drive mechanism, which is coupled to a robotic arm, can be coupled to a medical instrument in order to control movement and/or actuation of the medical instrument. The drive mechanism includes a number of motor-driven output shafts which are coupled to a corresponding number of inputs of the medical instrument configured to receive the output shafts of the drive mechanism. When coupling the medical instrument to the drive mechanism, it may be desirable to align the medical instrument inputs with the output shafts, thereby enabling the inputs on the medical instrument to be driven by the output shafts of the drive mechanism.

SUMMARY

The systems, methods and devices of this disclosure each have several innovative aspects, no single one of which is solely responsible for the desirable attributes disclosed herein.

In one aspect, there is provided a robotic medical system, comprising: an instrument drive mechanism, comprising: one or more output shafts, each of the one or more output shafts configured to mechanically couple with a corresponding input of a tool, wherein the tool comprises one or more pull wires configured to be actuated by the output shafts via the one or more inputs, one or more motors respectively coupled to the one or more output shafts and configured to rotate the corresponding one or more output shafts, and a data reader configured to receive alignment data from the tool when the tool is positioned within a threshold distance of the data reader; and at least one computer-readable memory in communication with at least one processor, the memory having stored thereon computer-executable instructions that cause the at least one processor to: receive the alignment data from the data reader, and rotate the one or more output shafts into alignment with the corresponding input of the tool based on the alignment data.

In another aspect, there is provided a tool, comprising: an end effector; one or more inputs configured to control actuation of the end effector, each of the one or more inputs configured to be mechanically coupled to a corresponding output shaft of a drive mechanism; one or one or more pull wires configured to be actuated by the one or more inputs to control actuation of the end effector; and a data transmitter configured to transmit alignment data to a data reader of the drive mechanism, wherein the transmission of the alignment data to the data reader of the drive mechanism is configured to facilitate the drive mechanism aligning the one or more output shafts with the one or more inputs.

In yet another aspect, there is provided a method of aligning an instrument drive mechanism with a tool, comprising: receiving, at a data reader of the instrument drive mechanism, alignment data from the tool when the tool is positioned within a threshold distance of the data reader, wherein the tool comprises one or more inputs and one or more pull wires configured to be actuated by output shafts of the instrument drive mechanism via the one or more inputs; receiving, at a processor, the alignment data from the data reader; and rotating, via the processor, the one or more output shafts of the instrument drive mechanism into alignment with the one or more inputs of the tool based on the alignment data, wherein each of the output shafts is configured to mechanically couple with a corresponding one of the inputs of the tool.

In still yet another aspect, there is provided a method of aligning a drive mechanism with a tool, comprising: transmitting alignment data from a data transmitter of the tool to a data reader of the drive mechanism to facilitate the drive mechanism aligning one or more output shafts of the drive mechanism with one or more inputs of the tool, wherein the tool comprises one or one or more pull wires configured to be actuated by the one or more inputs to control actuation of an end effector, and wherein each of the one or more inputs is configured to be mechanically coupled to a corresponding one of the output shafts of the drive mechanism.

In another aspect, there is provided a non-transitory computer readable storage medium having stored thereon instructions that, when executed, cause at least one computing device to: receive, at a data reader of an instrument drive mechanism, alignment data from a tool when the tool is positioned within a threshold distance of the data reader, wherein the tool comprises one or more inputs and one or more pull wires configured to be actuated by output shafts of the instrument drive mechanism via the one or more inputs; receive, at the computing device, the alignment data from the data reader; and rotate the one or more output shafts of the instrument drive mechanism into alignment with the one or more inputs of the tool based on the alignment data, wherein each of the output shafts is configured to mechanically couple with a corresponding one of the inputs of the tool.

In yet another aspect, there is provided a non-transitory computer readable storage medium having stored thereon instructions that, when executed, cause at least one computing device to: transmit alignment data from a data transmitter of a tool to a data reader of a drive mechanism to facilitate the drive mechanism aligning one or more output shafts of the drive mechanism with one or more inputs of the tool, wherein the tool comprises one or one or more pull wires configured to be actuated by the one or more inputs to control actuation of an end effector, and wherein each of the one or more inputs is configured to be mechanically coupled to a corresponding one of the output shafts of the drive mechanism.

In still yet another aspect, there is provided a method of facilitating alignment between one or more outputs of a drive mechanism with one or more inputs of a tool, comprising: loading the tool onto the drive mechanism, wherein loading comprises: moving the tool from a first position to a second position, wherein in the second position the one or more inputs of the tool are closer in distance to the one or more outputs of the drive mechanism than in the first position, and during transition of the tool from the first position to the second position, transmitting alignment information from the tool to the drive mechanism, the alignment information indicative of relative alignment between the one or more inputs of the tool and the one or more outputs of the drive mechanism.

In another aspect, there is provided a method of facilitating alignment between one or more outputs of a drive mechanism with one or more inputs of a tool comprising: loading the tool onto the drive mechanism, wherein the tool comprises a radio frequency identification (RFID) chip and the drive mechanism comprises an RFID reader, wherein loading the tool comprises the RFID reader reading information from the RFID tag to determine whether the one or more outputs of the drive mechanism are in working alignment with the one or more inputs of the tool.

In yet another aspect, there is provided a method of facilitating alignment between one or more outputs of a drive mechanism with one or more inputs of a tool comprising: loading the tool onto the drive mechanism, wherein the drive mechanism includes a sensor configured to monitor a distance of separation between the one or more outputs of the drive mechanism and the one or more inputs of the tool; and upon reaching a threshold distance of separation between the one or more outputs and the one or more inputs, using an RFID reader on the drive mechanism to read an RFID tag on the tool.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
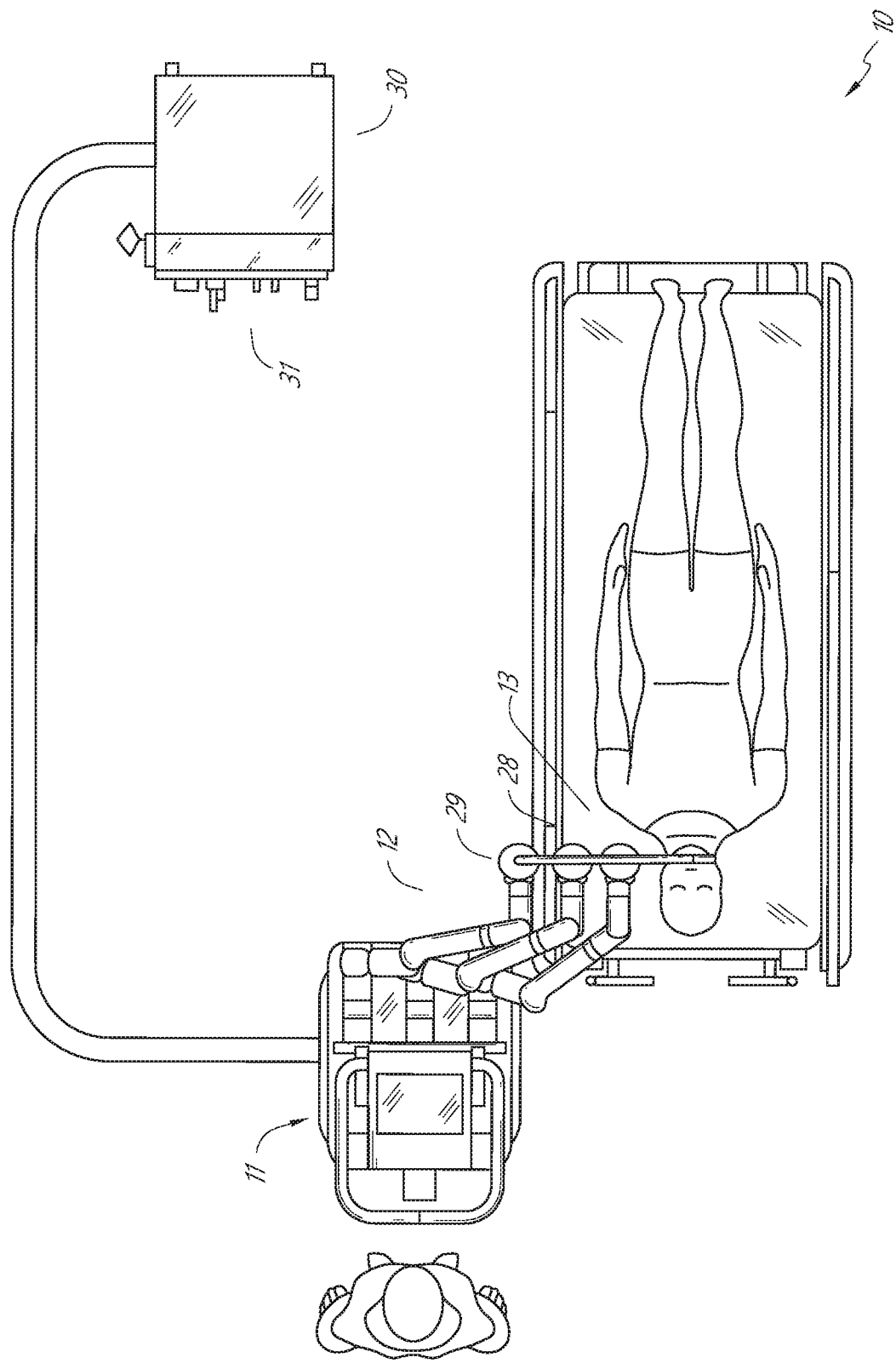
FIG. 1 illustrates an embodiment of a cart-based robotic system arranged for diagnostic and/or therapeutic bronchoscopy procedure(s).
Figure 2:
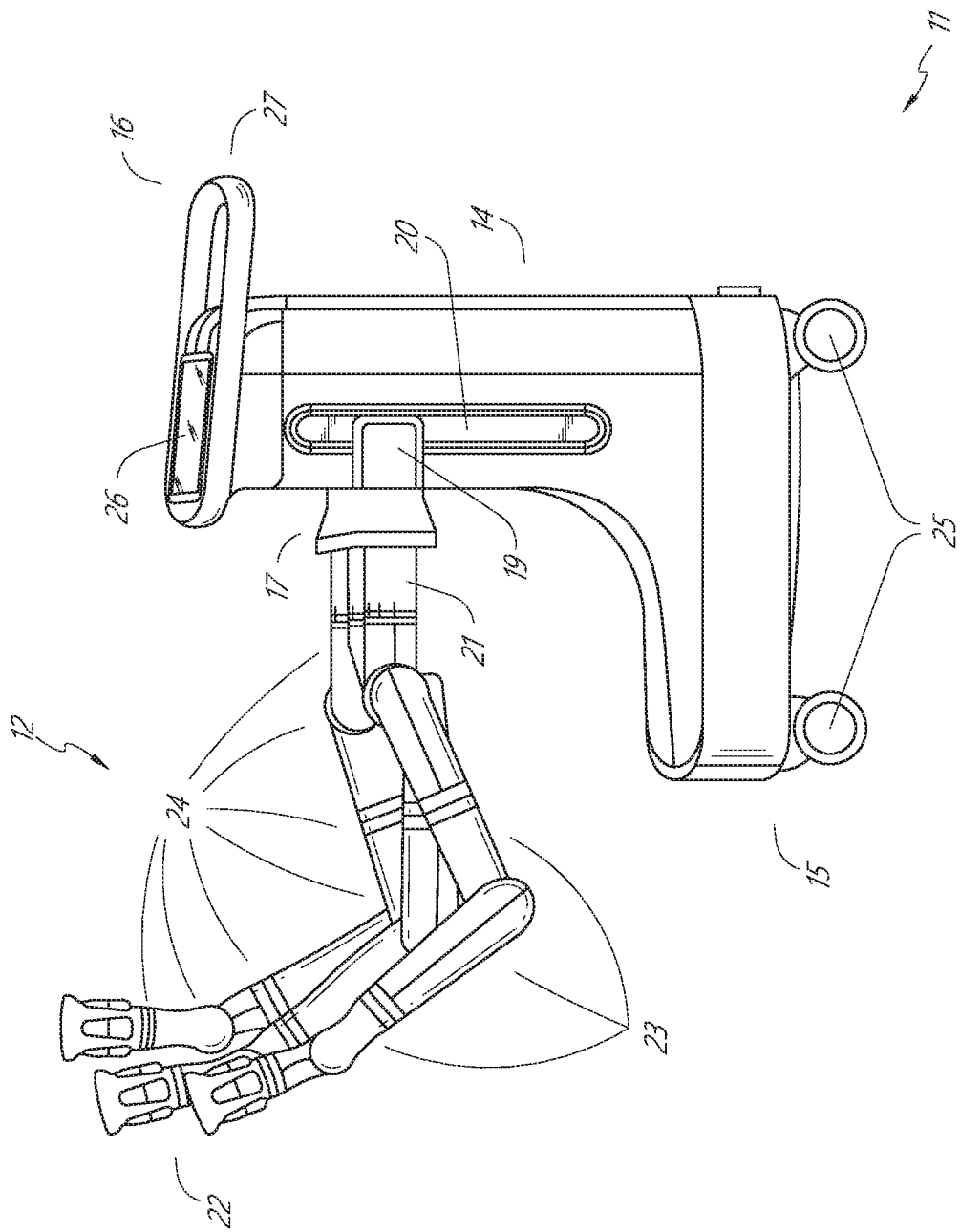
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
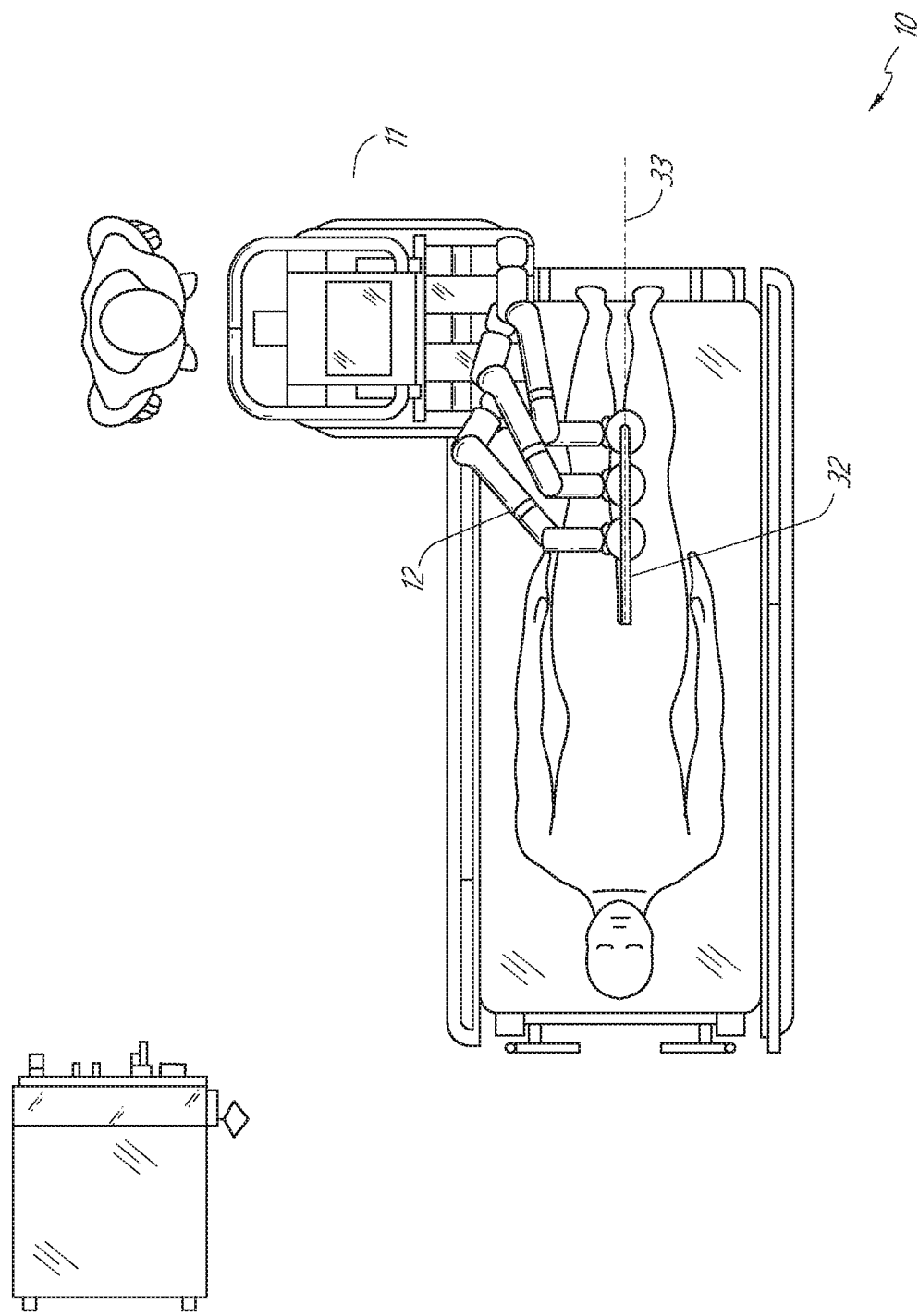
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
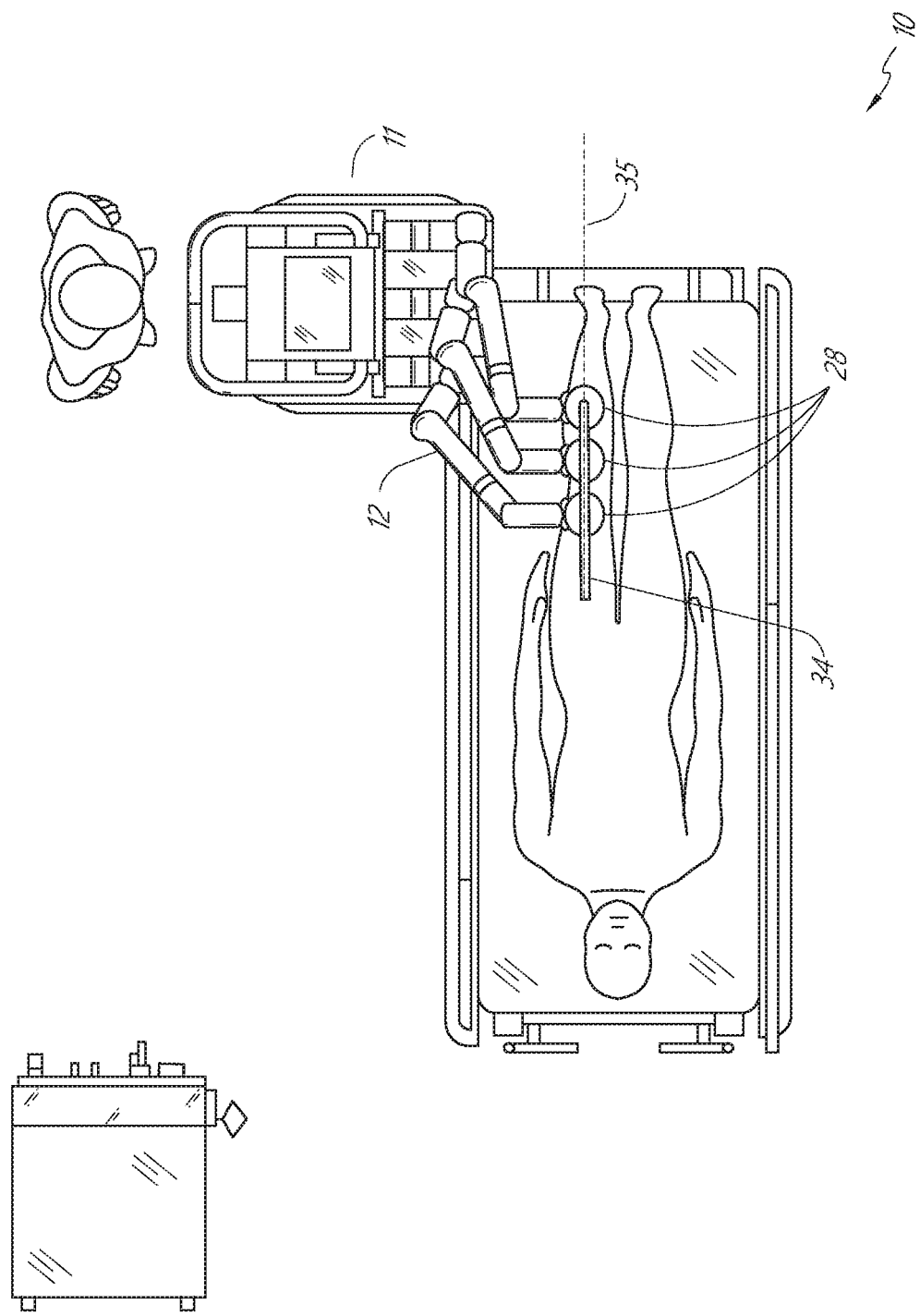
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
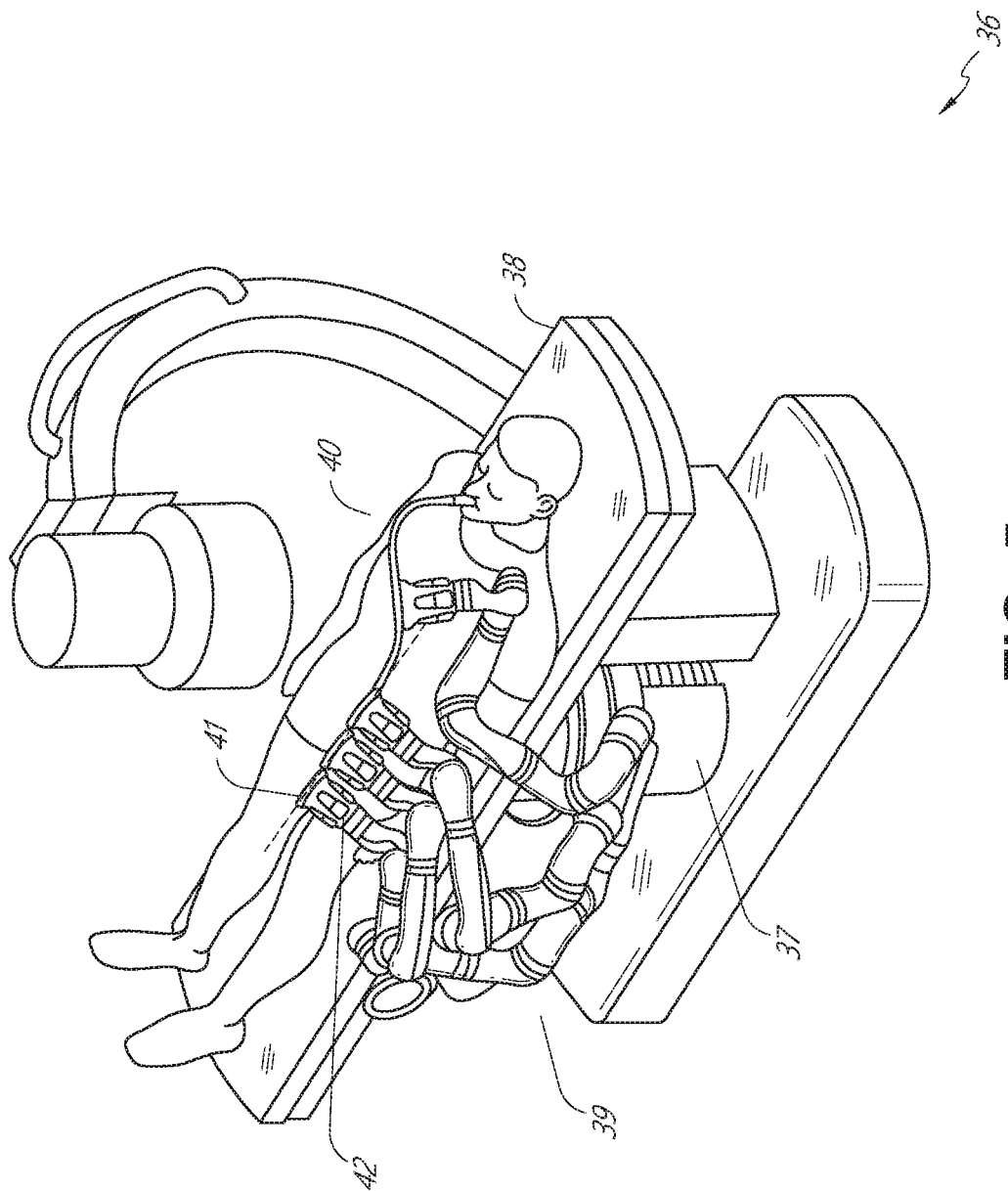
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
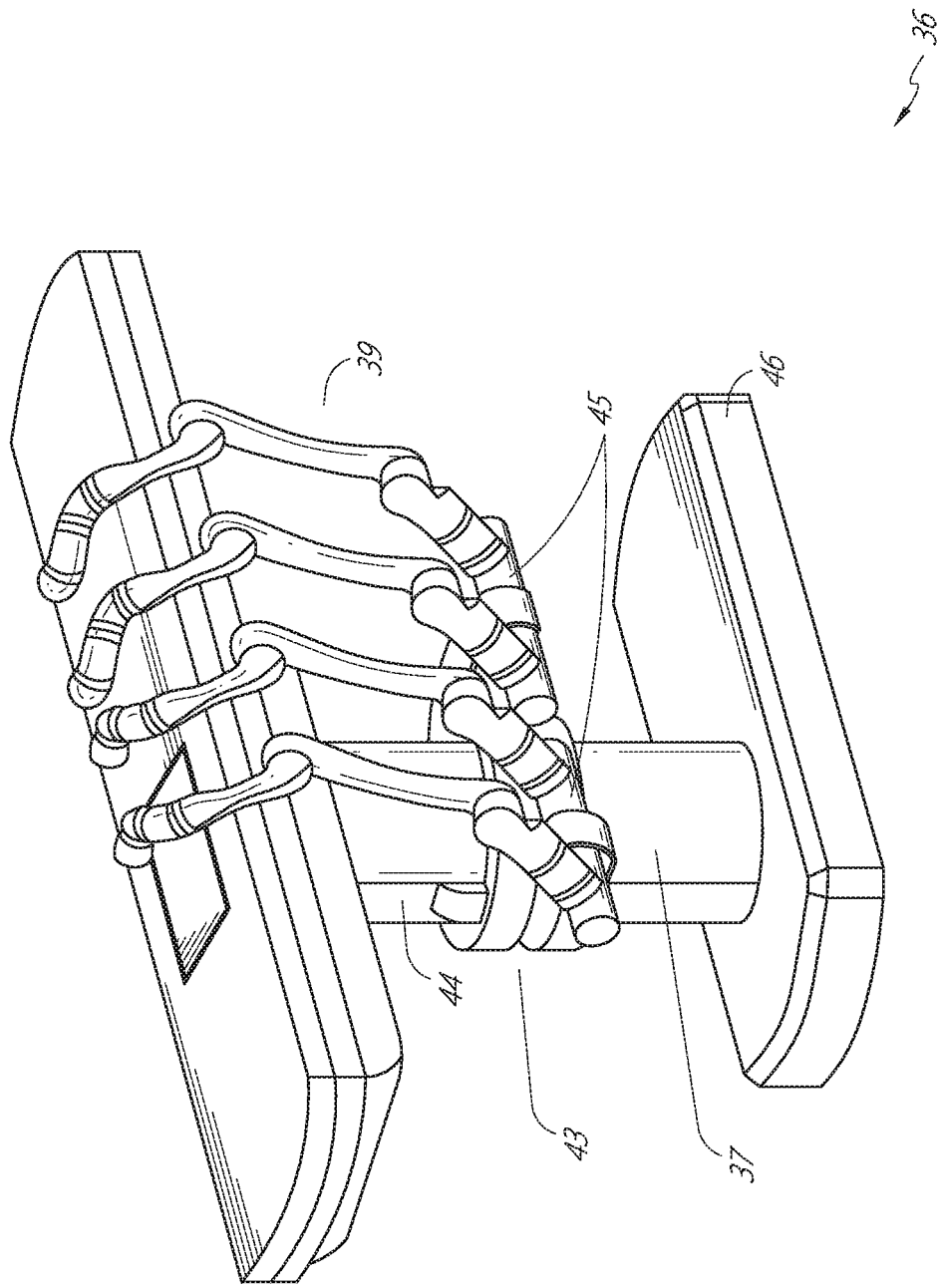
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
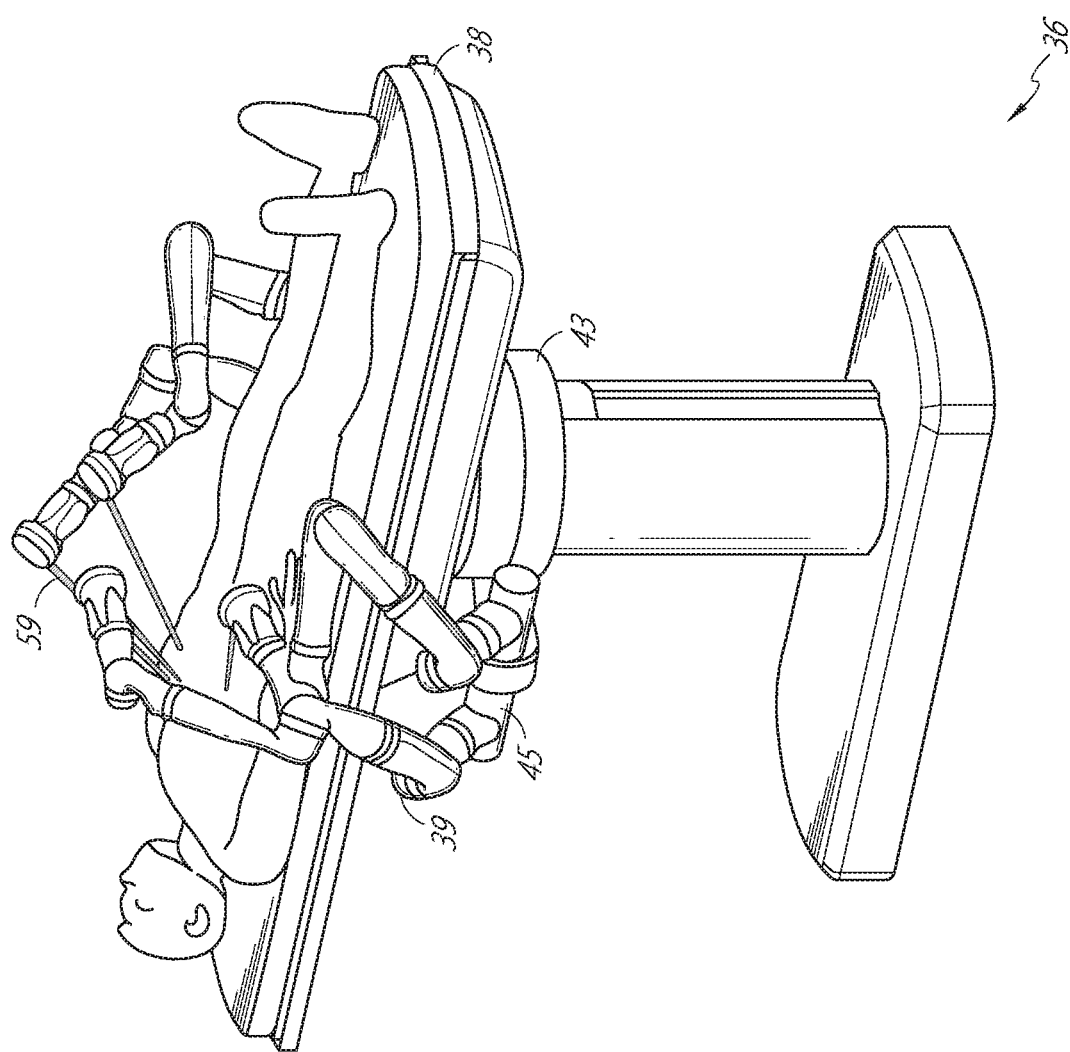
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
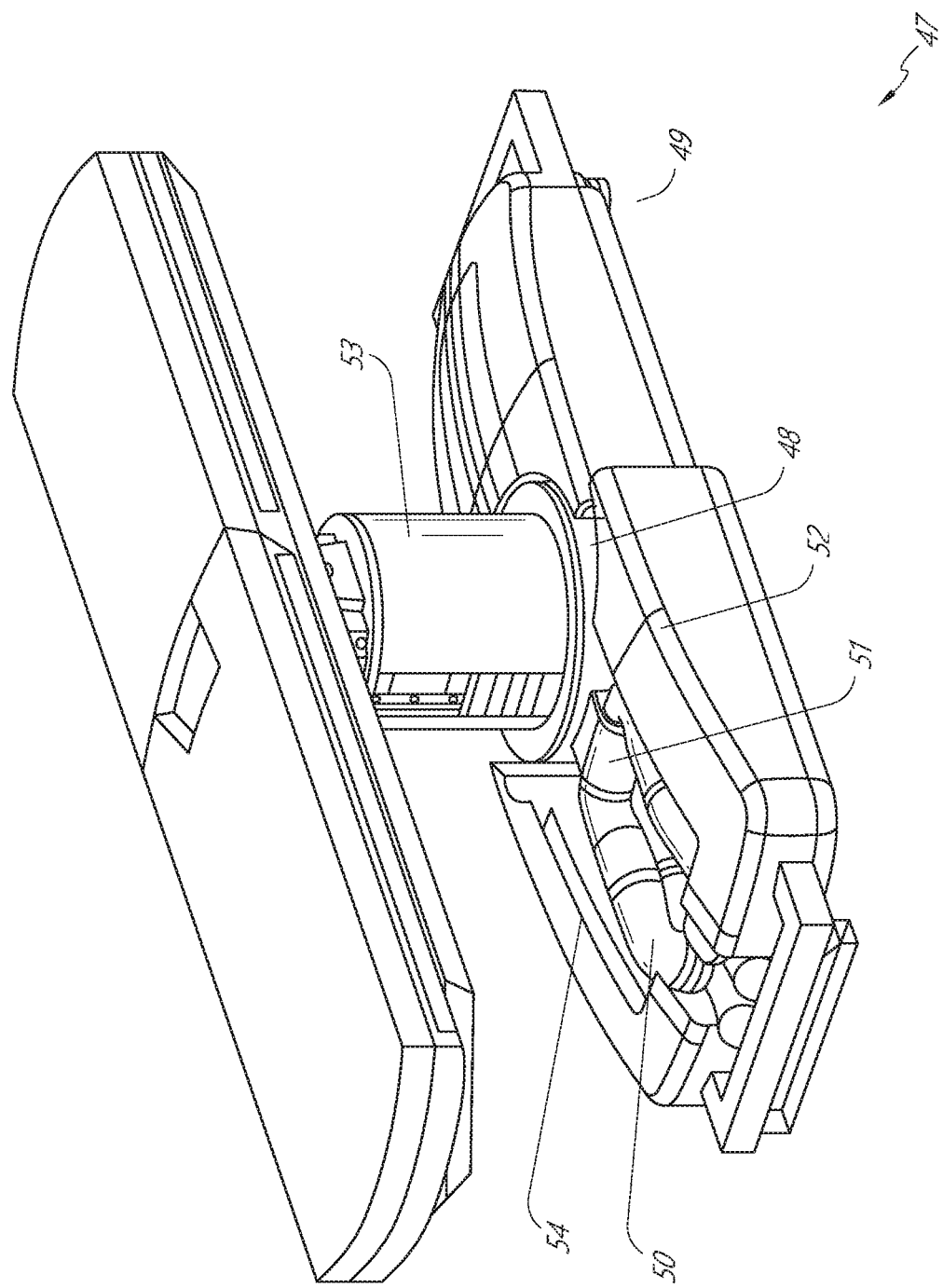
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
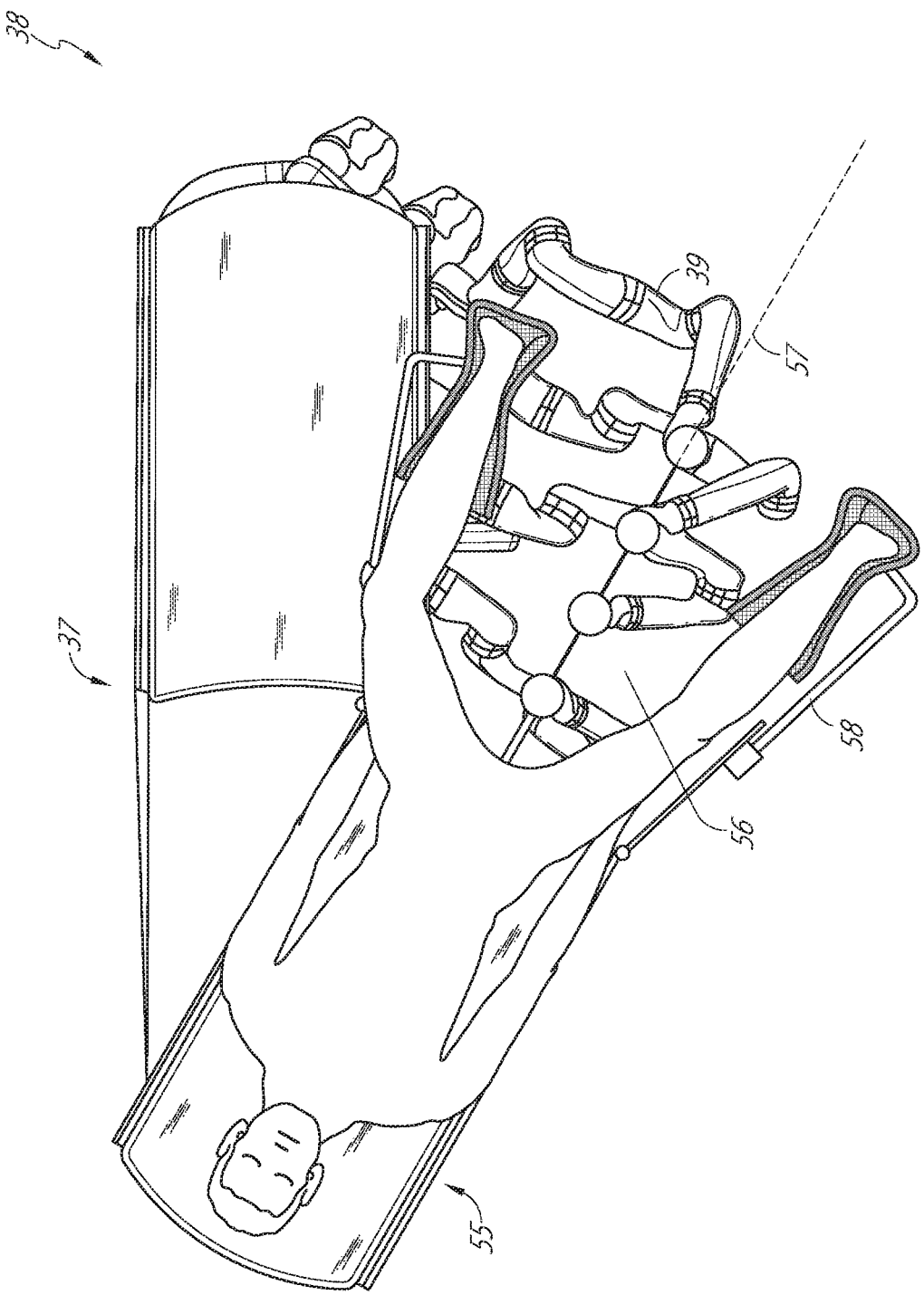
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
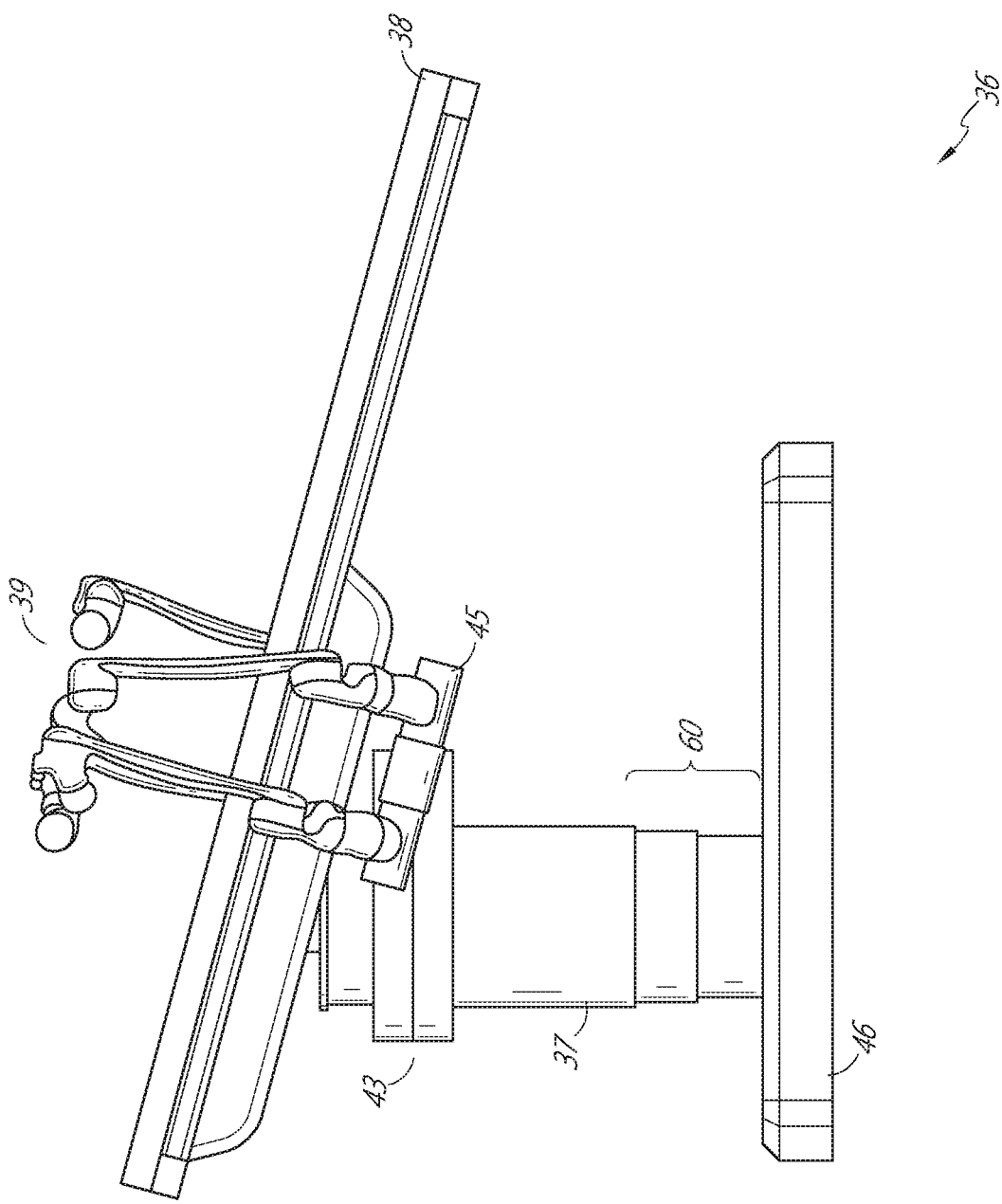
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
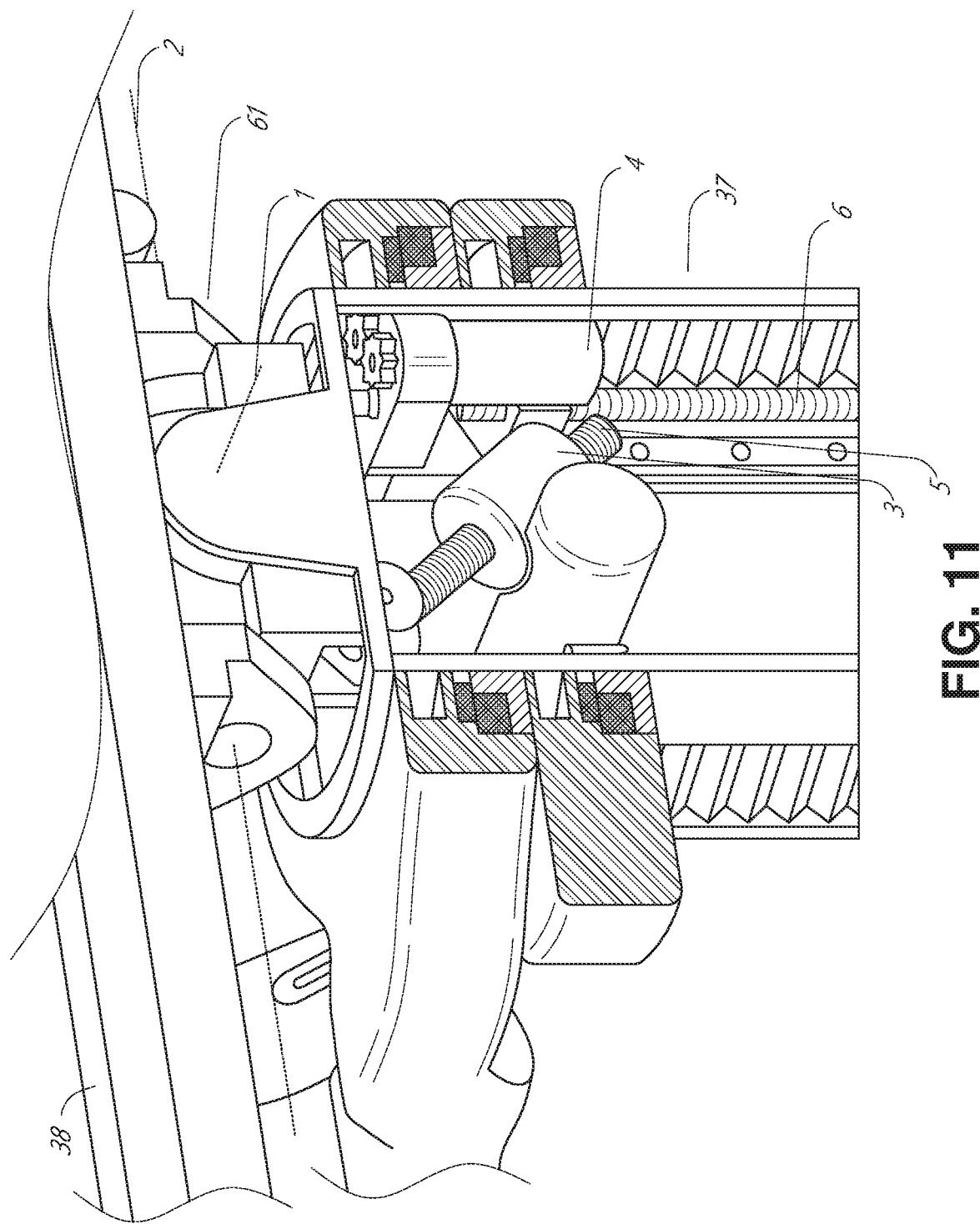
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
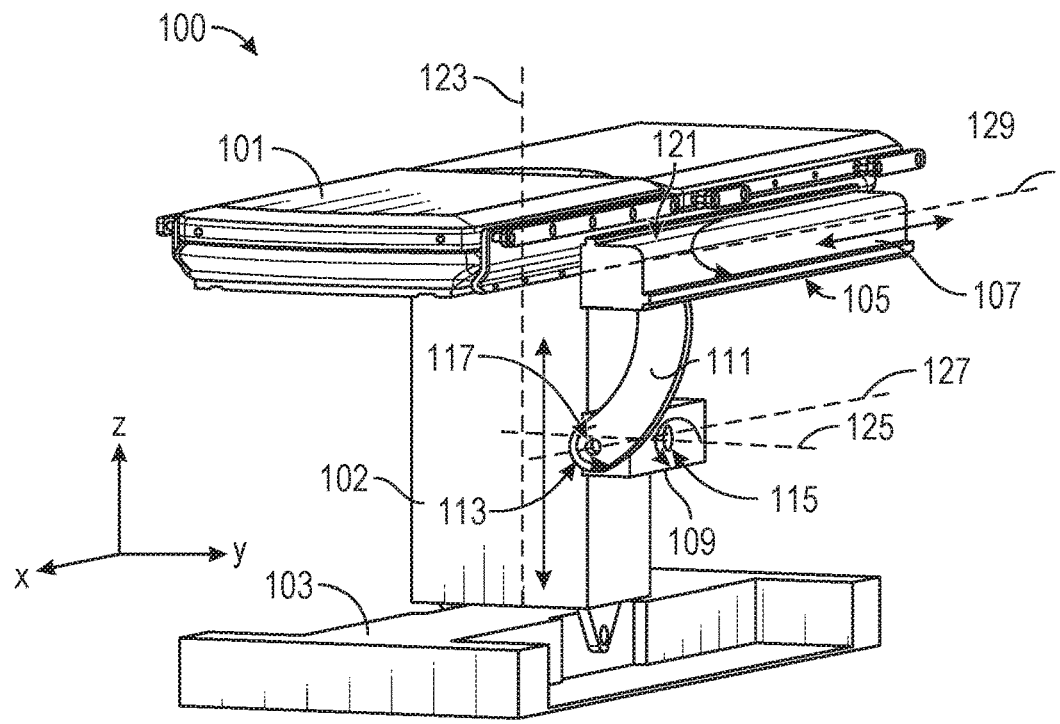
FIG. 12 illustrates an alternative embodiment of a table-based robotic system.
Figure 13:
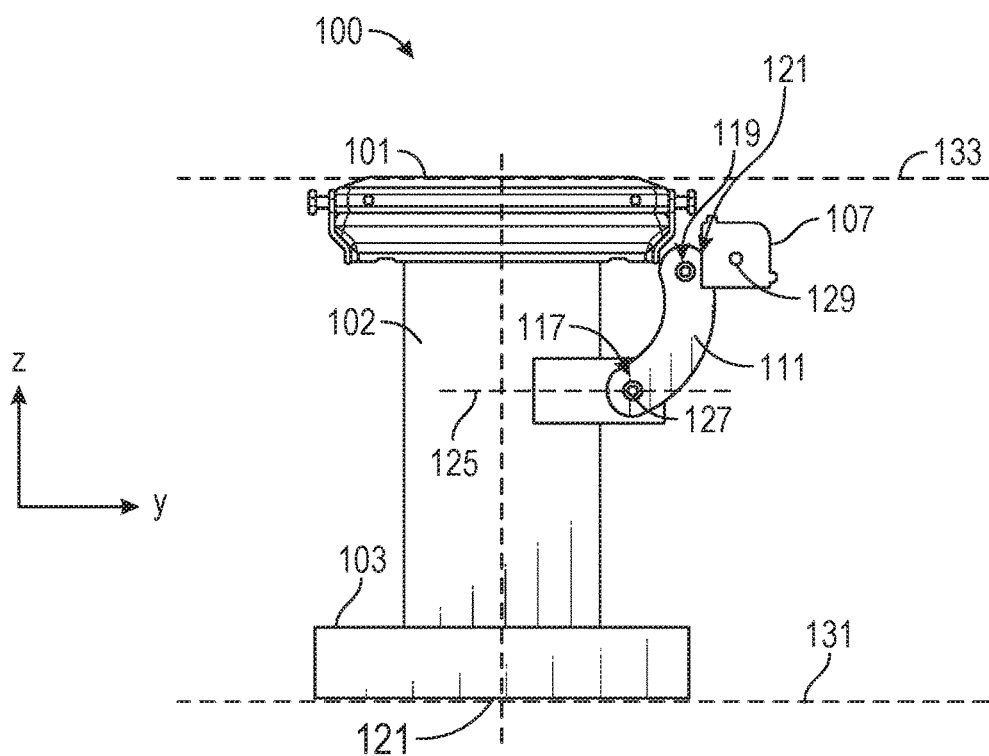
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom (Z-lift) to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
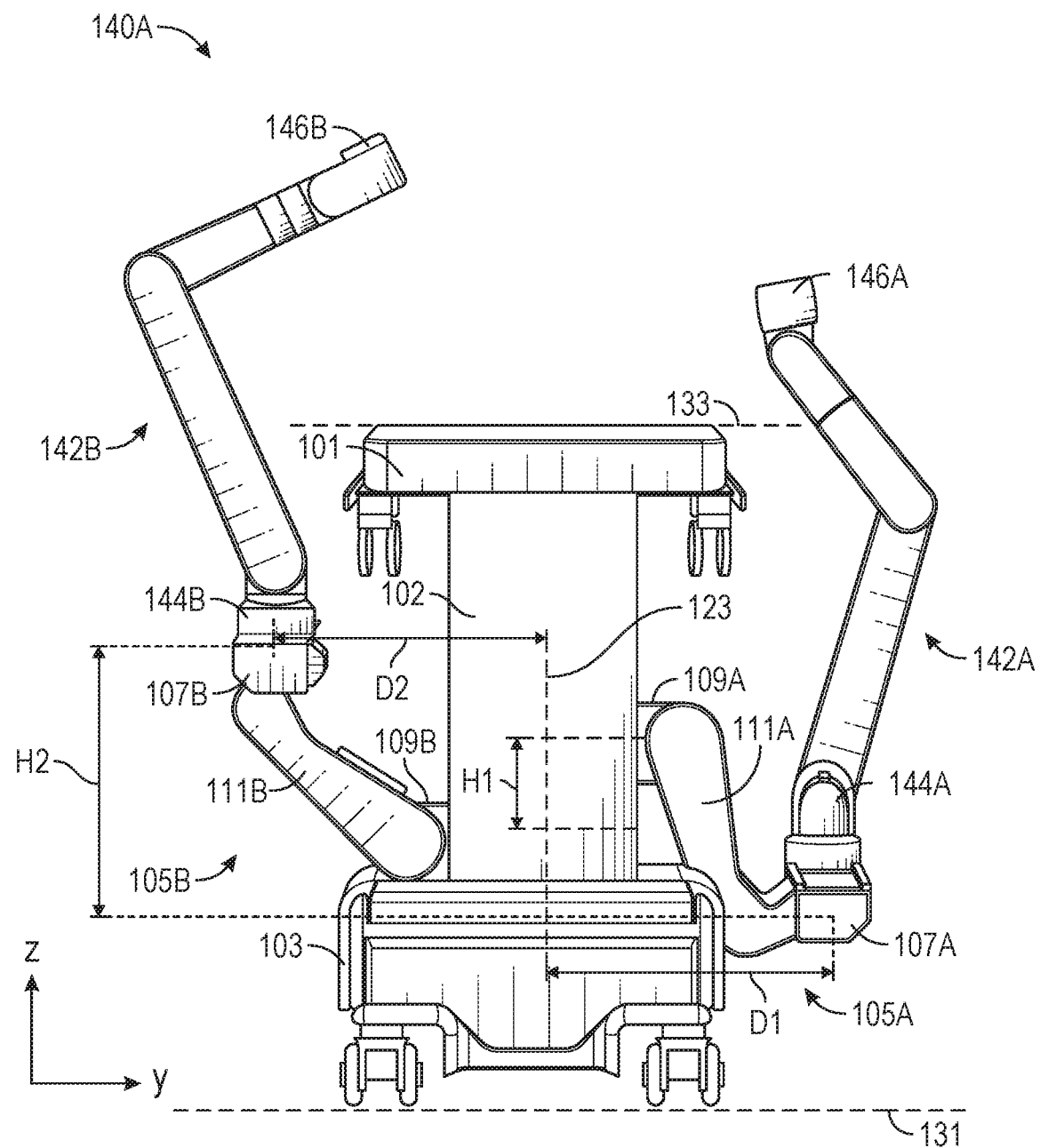
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
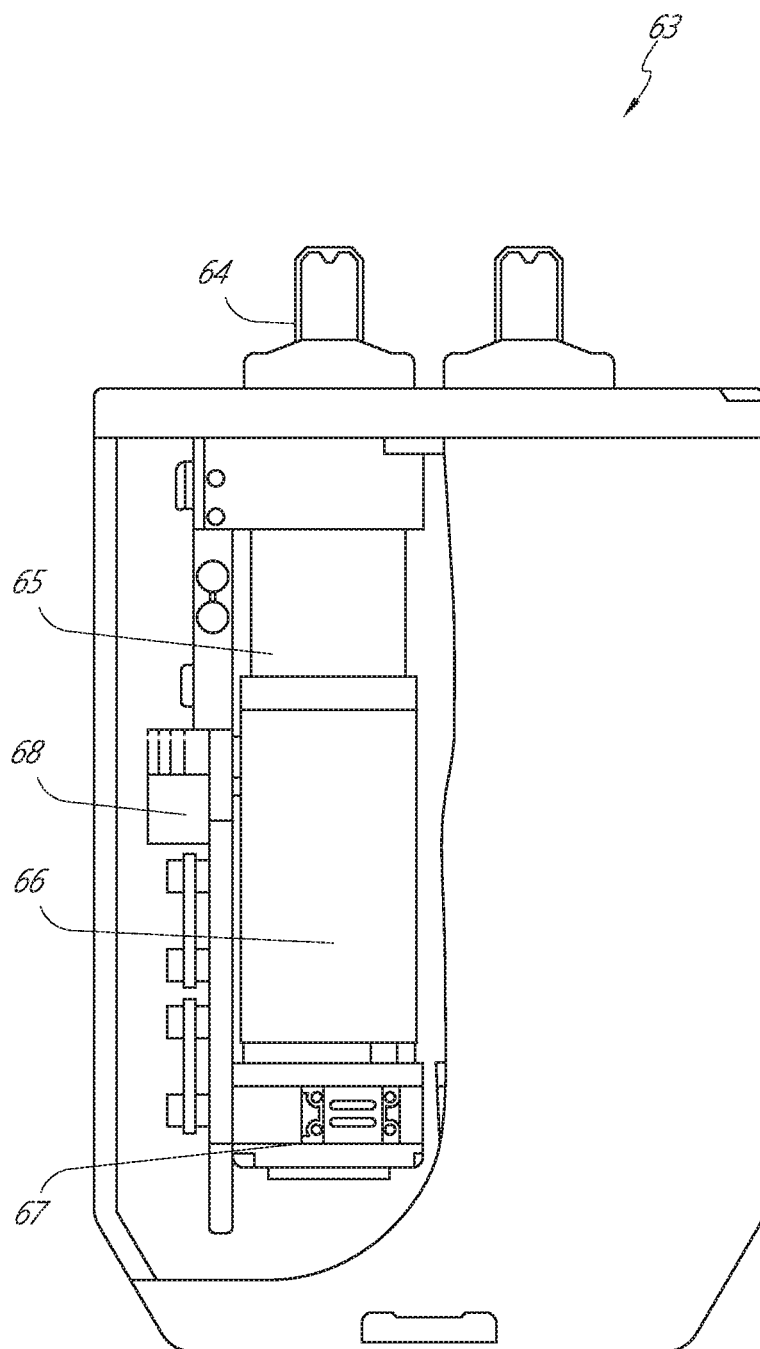
FIG. 15 illustrates an exemplary instrument driver.

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuity 68 for receiving control signals and actuating the drive unit. Each drive unit 63 being independent controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
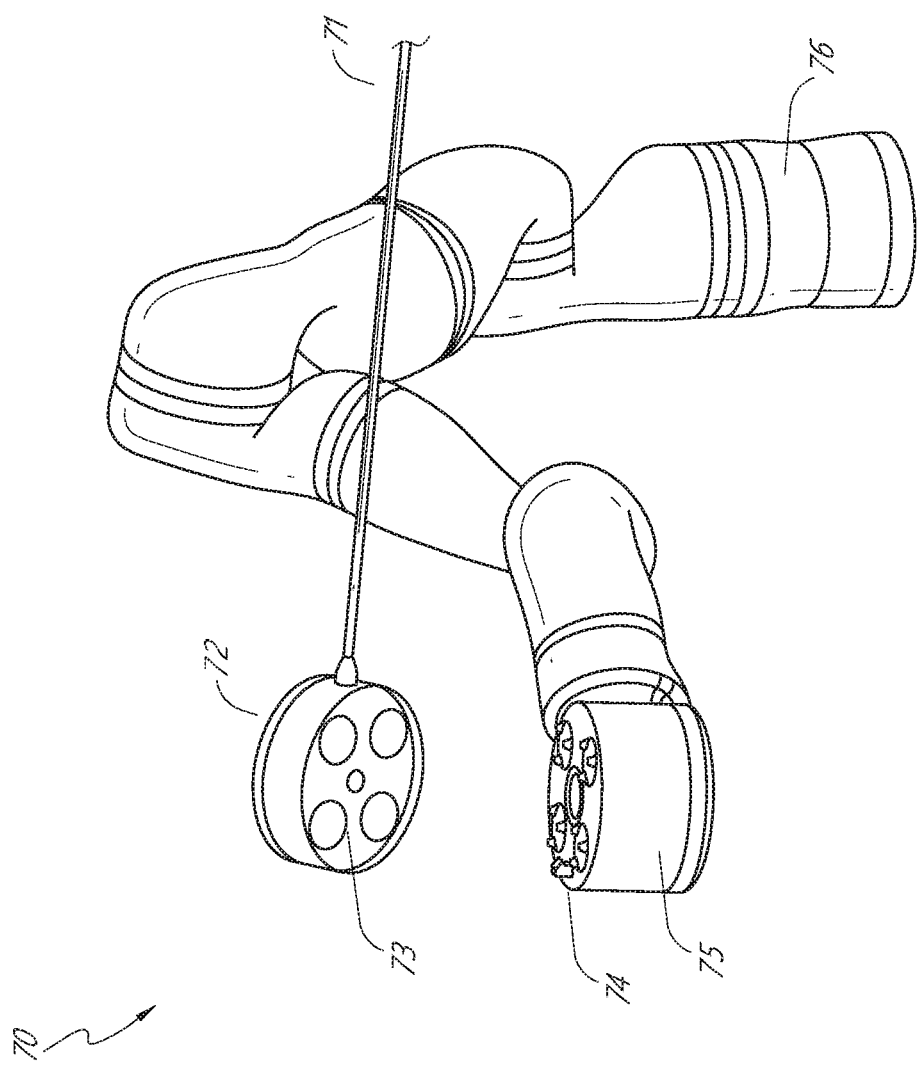
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
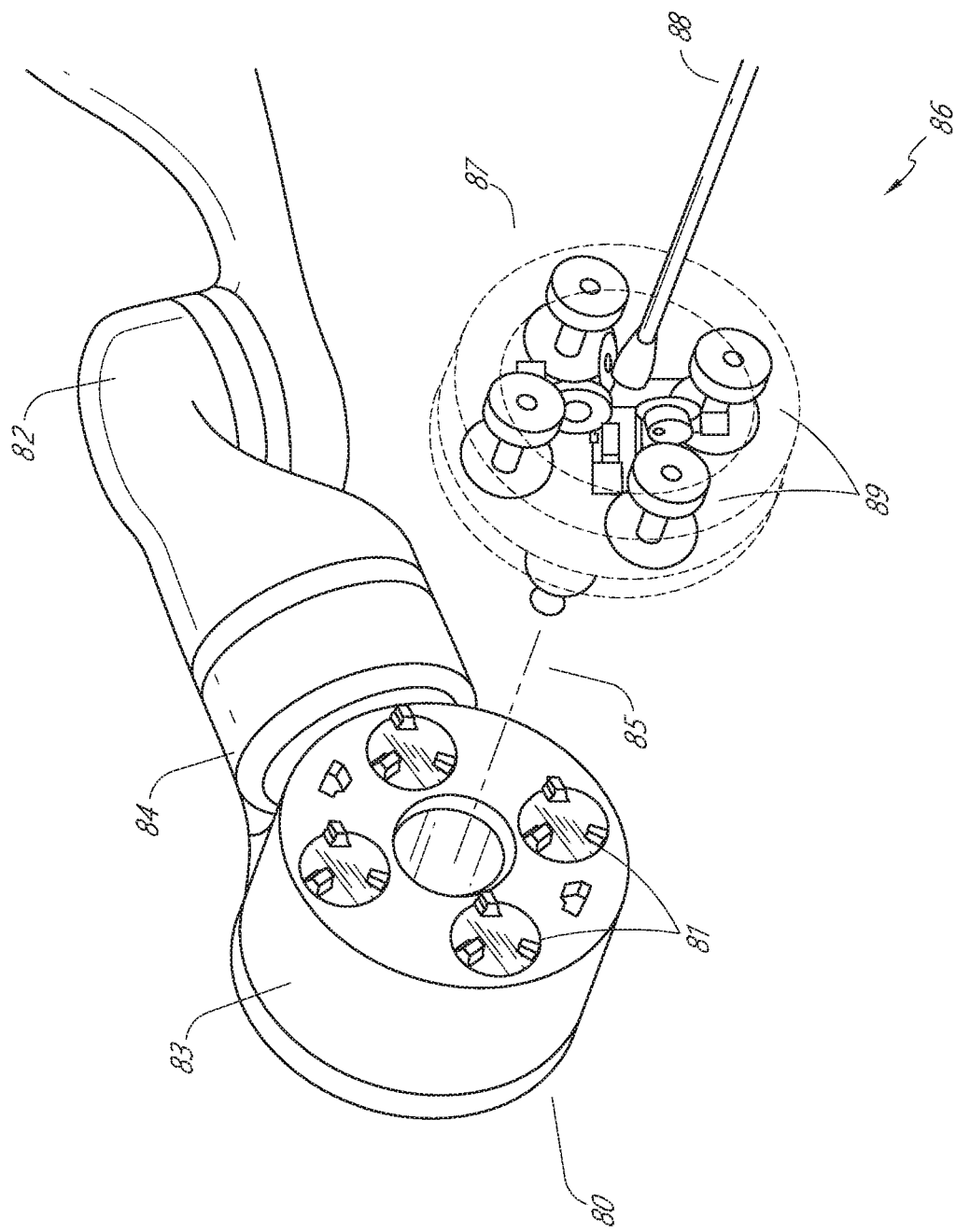
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
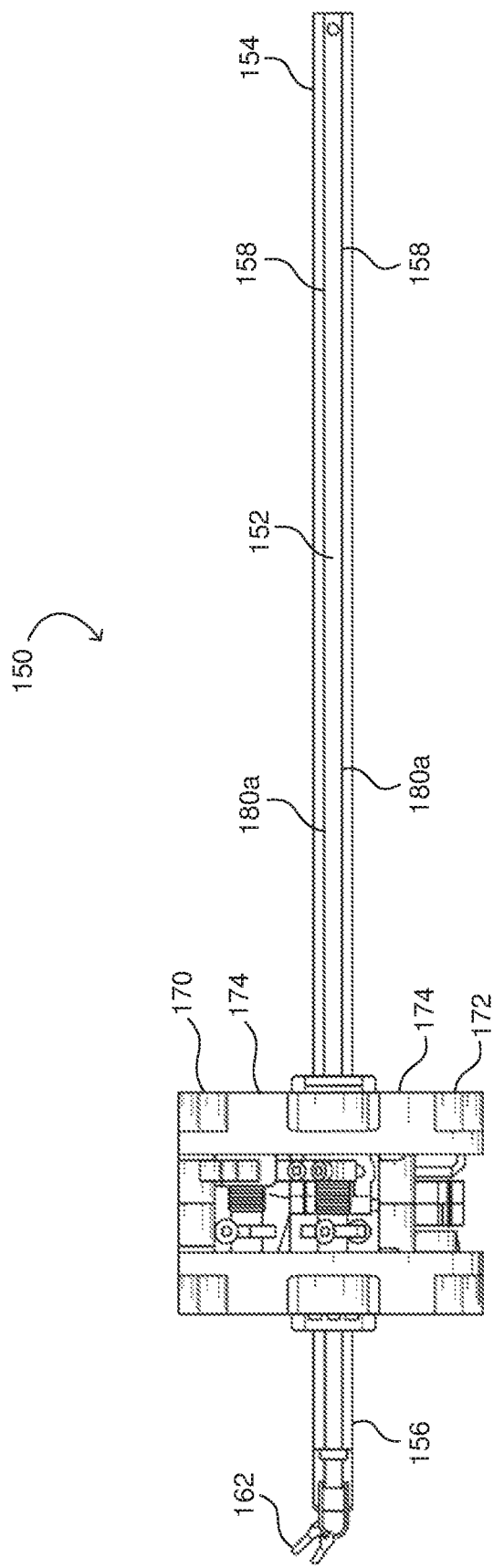
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
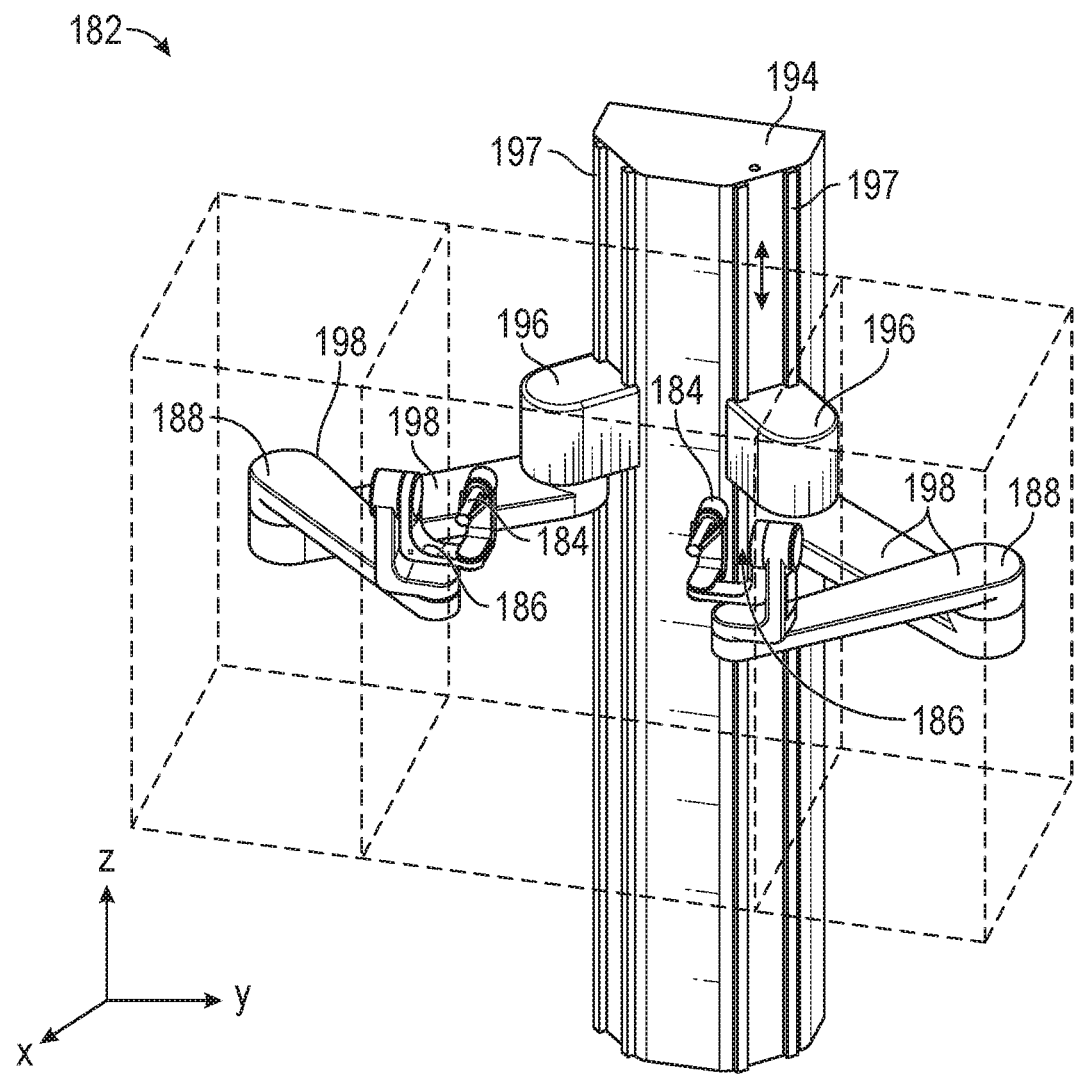
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
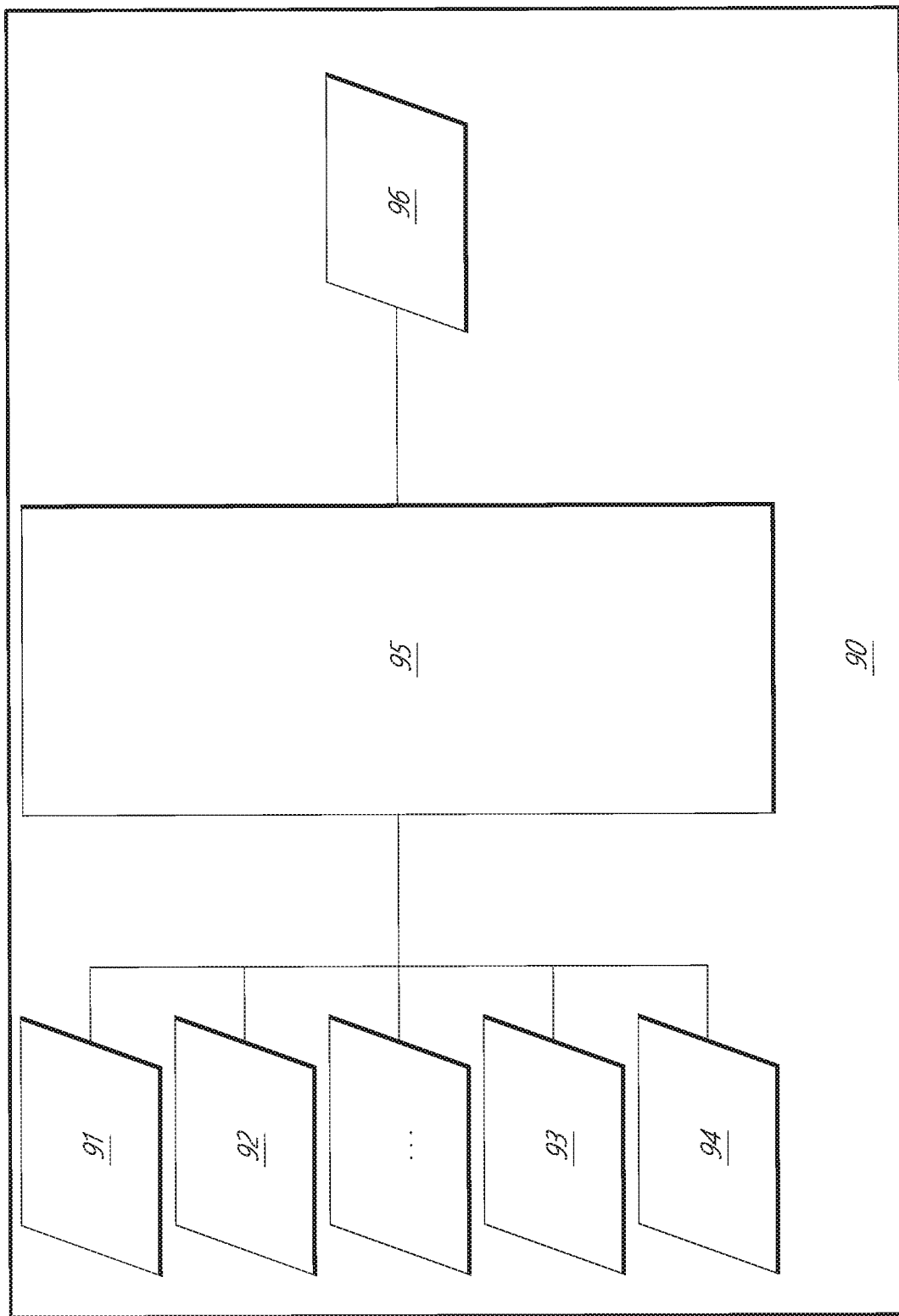
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction to Alignment of Medical Instrument Inputs.

Embodiments of the disclosure relate to systems and techniques for aligning inputs on a medical instrument with corresponding output shafts on a drive mechanism (e.g., an instrument drive mechanism (IDM) or an active drive mechanism (ADM)). One example medical procedure which may involve alignment of a medical instrument's inputs to output shafts on a drive mechanism is a laparoscopic procedure. For example, one or more laparoscopic tools (e.g., camera or other instrumentation) having an input may have to be aligned with corresponding output shafts of a drive mechanism to perform a medical procedure. However, aspects of this disclosure are not limited to alignment in a laparoscopic procedure, and may be applied to other medical procedures such as an endoscopic procedure (e.g., bronchoscopy, ureteroscopy, gastroscopy, etc.).

Figure 21:
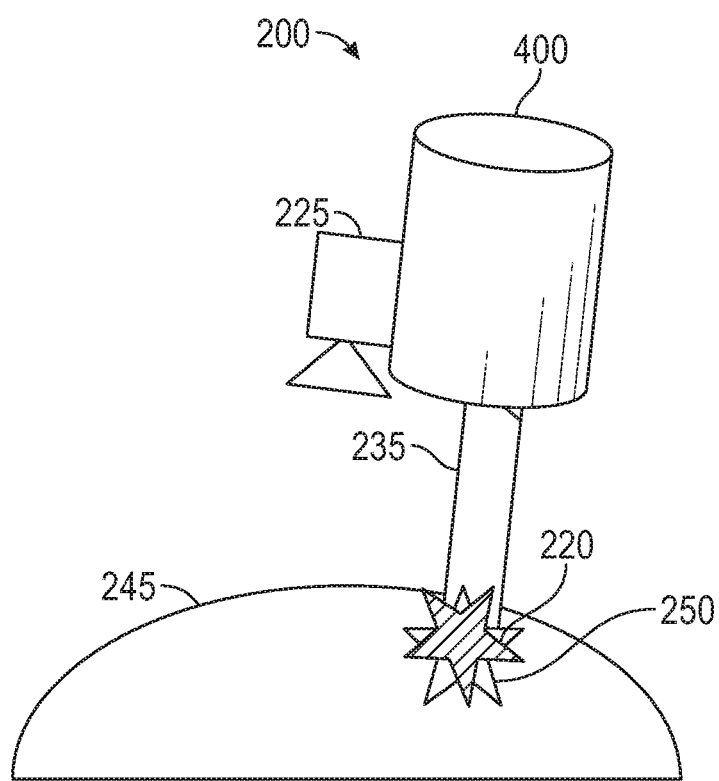
FIG. 21 illustrates an embodiment of a system configured for a laparoscopic procedure in accordance with aspects of this disclosure.

During a laparoscopic procedure, one or more cannulas for receiving a laparoscopic medical instrument (also referred to as a laparoscopic tool) can be inserted into a patient. FIG. 21 illustrates an embodiment of a system 200 configured for a laparoscopic procedure in accordance with aspects of this disclosure. The system 200 includes a drive mechanism 400 and a port or cannula 235. The drive mechanism 400 is configured to attach or couple to an instrument (not illustrated), which can then be actuated by the drive mechanism 400. The cannula 220 may be installed in a patient 245 through the patient's 245 body wall 250. Thus, the drive mechanism 400, which is coupled to a robotic arm (not illustrated), can be docked to the cannula 235 as shown in FIG. 21. The drive mechanism 400 may further comprise an optional camera 225, which can be configured to aid in aligning the drive mechanism 400 with the cannula 235 and/or alignment of one or more inputs of a medical instrument with one or more output shafts on the drive mechanism 400 as discussed below.

The system 200 may be configured to maintain a remote center of motion 220 in substantially the same location where the cannula 235 intersects the body wall 250. As used herein, the remote center of motion 220 may refer to a point in space at which the system 220 prevents motion of the cannula 235 and the laparoscopic tool (not illustrated) inserted through the cannula 235. In other words, the system 200 prevents movement of the cannula 220 at the remote center of motion 220 to prevent unnecessary forces from being applied to the body wall 250.

Figure 22:
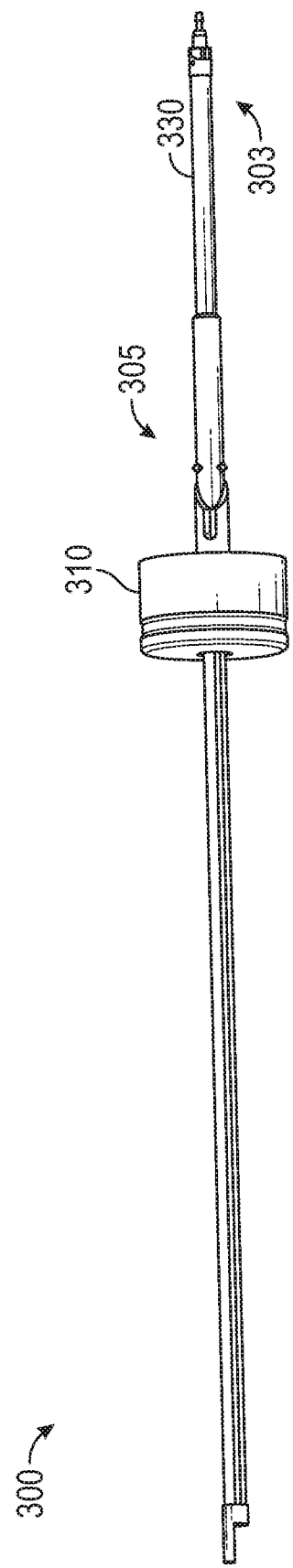
FIG. 22 illustrates an embodiment of a medical tool in accordance with aspects of this disclosure.

FIG. 22 illustrates an embodiment of a medical tool 300 in accordance with aspects of this disclosure. The tool 300 includes a handle 310, an alignment mechanism 305, a shaft 330, and an end effector 303. Although not illustrated, the tool 300 further includes one or more pull wires which are configured to be actuated via one or more inputs formed on the handle, which are described in greater detail below.

Figure 23A:
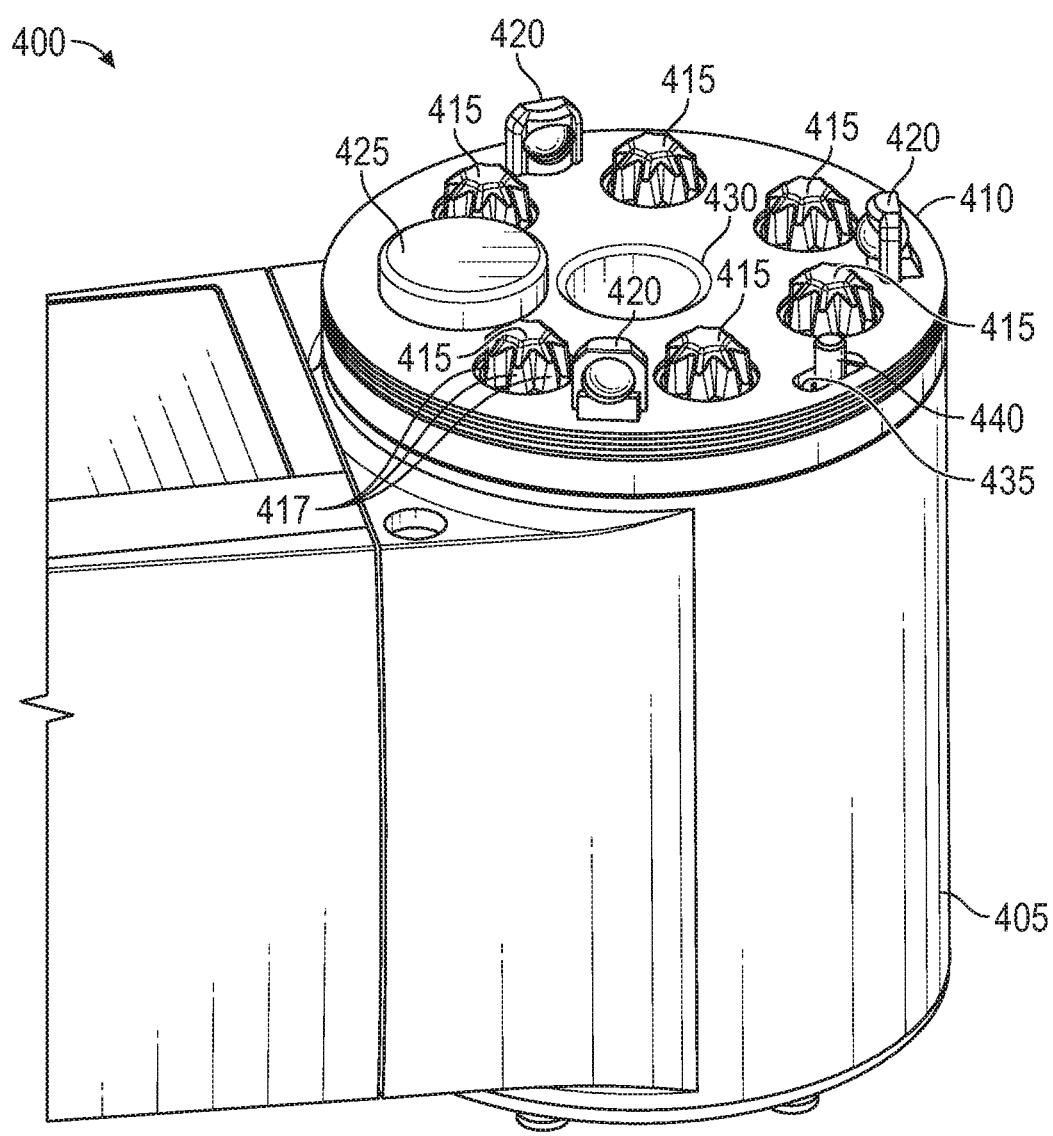
FIG. 23A illustrates an embodiment of a drive mechanism in accordance with aspects of this disclosure.
Figure 23B:
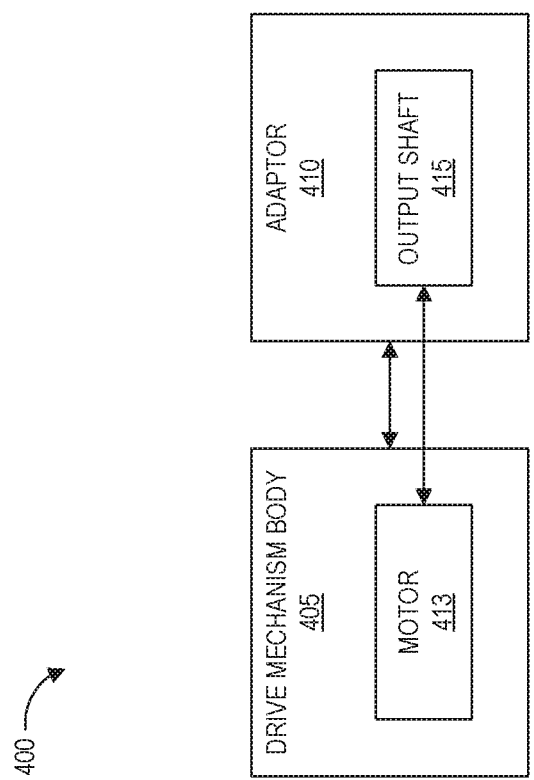
FIG. 23B is a schematic illustration showing how the drive mechanism can be coupled with an adaptor in accordance with aspects of this disclosure.

FIG. 23A illustrates an embodiment of a drive mechanism 400 in accordance with aspects of this disclosure. FIG. 23B is a schematic illustration showing how the drive mechanism 400 can be coupled with an adaptor 410 in accordance with aspects of this disclosure. With reference to FIGS. 23A-23B, the drive mechanism 400 includes a drive mechanism body 405, which may be coupled to the adaptor 410. The drive mechanism body 405 may be coupled to a robotic arm (e.g., the robotic arm 12 of FIG. 1 or the robotic arm 39 of FIG. 5) configured to control actuation of certain components of the drive mechanism 400. The adaptor 410 may form an interface between the drive mechanism 400 and the medical tool 300. In certain embodiments, the medical tool 300 can be directly coupled to the drive mechanism 400 without the use of an adaptor. In these embodiments, the various components/feature of the adaptor 410 (described below) may be formed on an upper surface of the drive mechanism 400 itself.

The adaptor 410 may be part of, for example, a sterile drape that covers one or more sterile component(s) of a surgical robotic system and the IDM 400 and may facilitate maintaining a sterile interface between the drive mechanism 400 and one or more components of the robotic arm or medical tool 300, thereby providing a barrier between non-sterile component(s) of the robotic system and a sterile surgical zone or area.

The adaptor 410 includes a plurality of output shafts 415, a plurality of attachment mechanisms 420, a reader housing 425, a channel 430, and a release slot 435 through which an adaptor release mechanism 440 of the drive mechanism 400 can extend. Each of the output shafts 415 are configured to engage with a corresponding input (e.g., see FIG. 24) of the handle 310 of the tool 300. As noted in the schematic illustration of FIG. 23B, the drive mechanism 400 further comprises a plurality of motors 413 respectively coupled to the output shafts 415. The motors 413 are configured to engage with and rotate the corresponding output shafts 415 of the adaptor 410. In embodiments where the output shafts 415 are formed as a component of the drive mechanism body 405, the motors 413 may be directly mechanically coupled to the output shafts 415.

The attachment mechanisms 420 are configured to provide a secure connection between the medical tool 300 and the instrument drive mechanism 400 via the adapter 410. In some embodiments, the attachment mechanisms 420 can include locking elements on the adapter 410 and corresponding pockets (e.g., see FIG. 24) on the medical tool 300. The reader housing 425 houses a data reader configured to receive alignment data from the tool 300 when the tool 300 is positioned within a threshold distance of the data reader. The channel 430 is configured to receive the shaft 330 of the tool 300. The adaptor 410 can be released from the drive mechanism 400 by actuation of the release mechanism 440, formed on the drive mechanism 400 and extending through the release slot 435 when the adaptor 410 is coupled to the drive mechanism 400.

Figure 24:
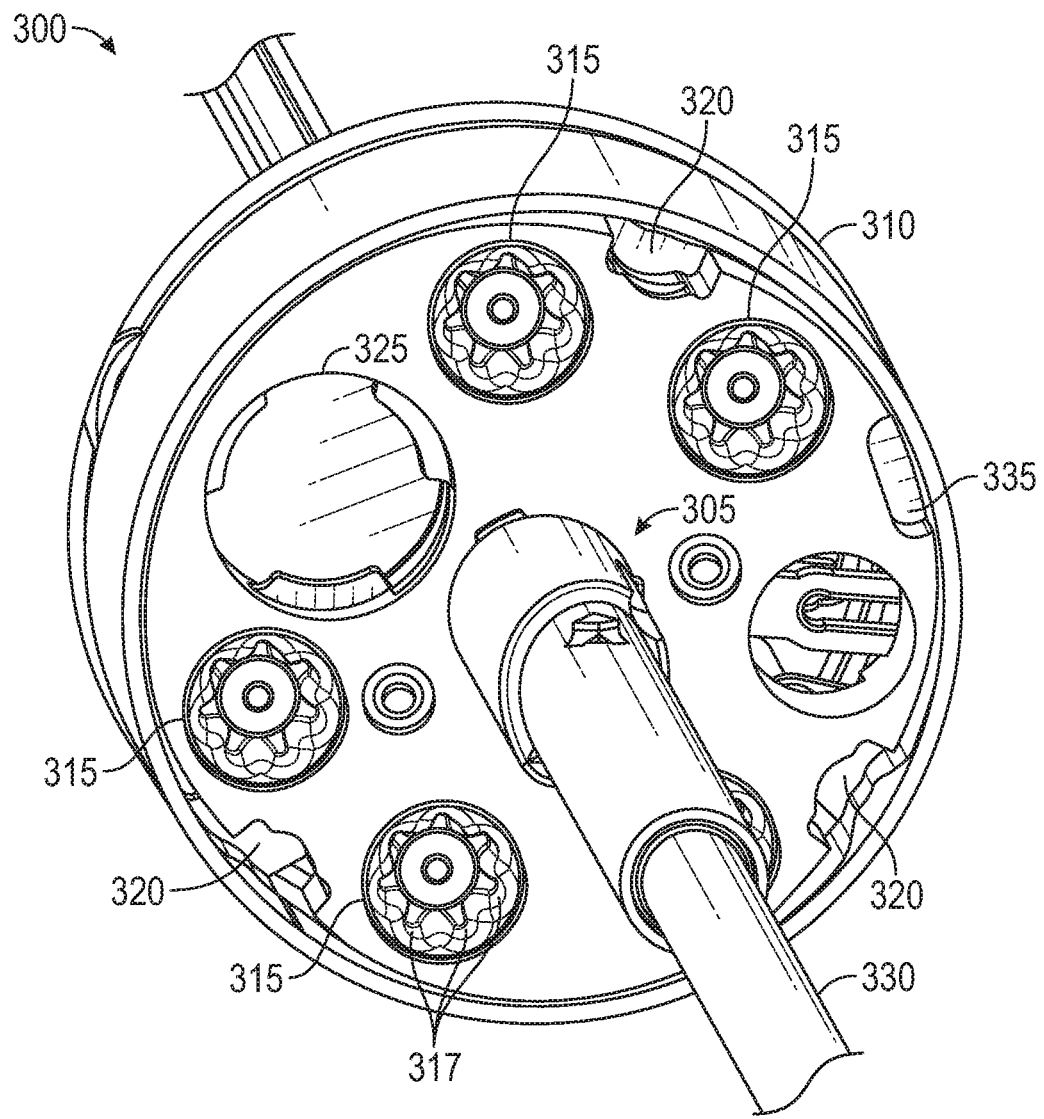
FIG. 24 illustrates an embodiment of the medical tool of FIG. 22 including an illustration of a lower surface of the handle in accordance with aspects of this disclosure.

FIG. 24 illustrates an embodiment of the medical tool 300 of FIG. 22 including an illustration of a lower surface of the handle 310 in accordance with aspects of this disclosure. In particular, the medical tool 300 includes the handle 310 from which the shaft 330 and the alignment mechanism 305 extend. The handle 310 includes a plurality of inputs 315 (also referred to as drive inputs), a plurality of pockets 320, and a recess 325. As previously described, the inputs 315 are configured to be mechanically coupled to and engage with the output shafts 415 of the adaptor 410 and drive mechanism 400. The tool 300 further includes a plurality of pull wires configured to be actuated by the output shafts 415 via the inputs 315 so as to control actuation of the end effector 303. In other words, each of the inputs 315 is configured to be mechanically coupled to a corresponding one of the output shafts 415 of the drive mechanism 400 (e.g., via the adaptor 410).

The pockets 320 are configured to engage with and receive the attachment mechanisms 420 so as to mechanically couple the handle 310 to the adaptor 410. The recess 325 provides a space for the reader housing 425 to be accommodated while the tool 300 is coupled to the drive mechanism 400. In some embodiments, as described below, the recess 325 further includes a wireless data transmitter configured to transmit alignment data wirelessly to a data reader housed within the reader housing 425. The alignment mechanism 305 is configured to provide proper orientation between the tool 300 and the drive mechanism 400 and adapter 410. The drive mechanism 440, adaptor 410, and handle 300 may have a similar configuration to those described in U.S. patent application Ser. No. 16/357,763, filed Mar. 19, 2019, the entirety of which is incorporated herein by reference.

Figure 25:
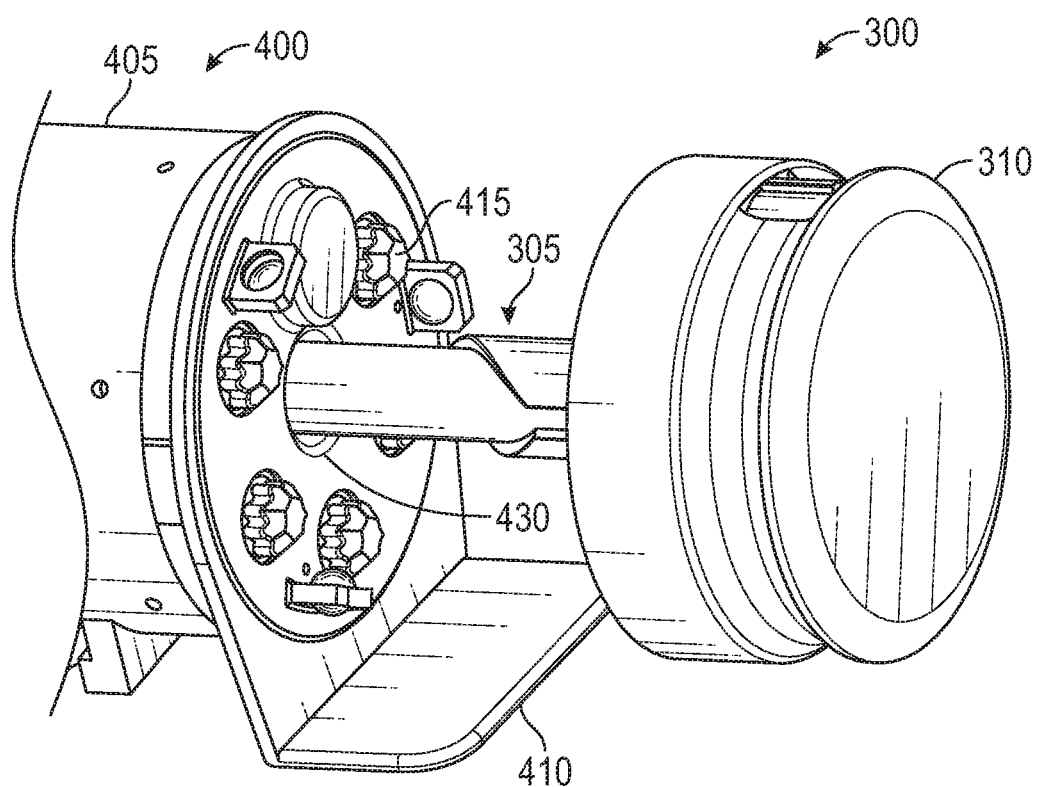
FIG. 25 illustrates the medical tool of FIG. 24 in the process of being coupled to the drive mechanism of FIG. 23A in accordance with aspects of this disclosure.

FIG. 25 illustrates the medical tool 300 of FIG. 24 in the process of being coupled to the drive mechanism 400 of FIG. 23A in accordance with aspects of this disclosure. As shown in FIG. 25, the alignment mechanism 305 may be inserted into the channel 430 of the adapter 410 as the handle 310 is advanced towards the drive mechanism 400 and adaptor 410. The alignment mechanism 305 may provide a mechanism reorientation of the handle 310 (e.g., rotation about the central axis of the tool 300) such that the components formed on the adaptor 410 (e.g., the output shafts 415, attachment mechanisms 420, and reader housing 425) align with the respective components of the handle 310 (e.g., the inputs 315, the pockets 320, and the recess 325).

As shown in FIGS. 23A-25, the output shafts 415 are formed to have male splines 417 that engage with corresponding female splines 317 formed in the inputs 315. As used herein, the term male spline may refer to ridges or teeth which can be formed on the output shafts 415 and are configured to couple to corresponding female splines 317 (e.g., grooves) formed on the inputs 315. Thus, the output shafts 415 and inputs 315 may form a plurality of spline couplings.

While FIGS. 23A-25 illustrate an embodiment in which the output shafts 415 having male splines 417 are formed on the adaptor 410 and the inputs 315 having female splines 317 are formed on the handle 310 of the tool 300, this disclosure is not limited thereto and various combinations of the output shafts 415, male splines 417, inputs 315, and female splines 317 can also be implemented. For example, in some embodiments, the output shafts may have female splines with the inputs having male splines and in other embodiments, the inputs may be formed on the adaptor and/or drive mechanism and the output shafts may be formed on the handle. In general, any combination may be possible such that rotational torque can be transferred from the drive mechanism to the tool, in order to actuate at least a portion of the tool (e.g., an end effector) in at least one degree of freedom.

Although the tool 300 has the alignment mechanism 305 that can generally align the outputs 315 of the drive mechanism 400 with the inputs 315 of the tool 300, there may still be misalignment between the male splines 417 formed on the output shafts 415 and the female splines 317 formed on the inputs 315 due to the discrete number of angles at which the splines can engage. While there may be some amount of allowable misalignment between the male and female splines 317, if the misalignment between the splines is greater than a threshold amount of misalignment, it can be difficult to couple the output shafts 415 to the inputs 315. The end effector 303 may be configured to be back driven by a certain amount (e.g., by back driving a wrist of the end effector) in order to align the inputs 315 with the output shafts 415. For example, the end effector can be forced through a certain range of articulation to rotate the inputs 315, thereby allowing some movement to aid in alignment. However, the range of motion provided by back driving can be limited by the amount of movement available for the wrist within a cannula and may force the inputs 315 to tension or detention in order to be installed on the output shafts 415, leading to a poor user experience. Thus, aspects of this disclosure relate to techniques for automatically aligning the output shafts 415 of a drive mechanism 400 with the inputs 315 of a tool 300, which may improve the user experience.

A. Automated Alignment of Medical Instrument Inputs with Drive Mechanism Output Shafts.

Figure 26A:
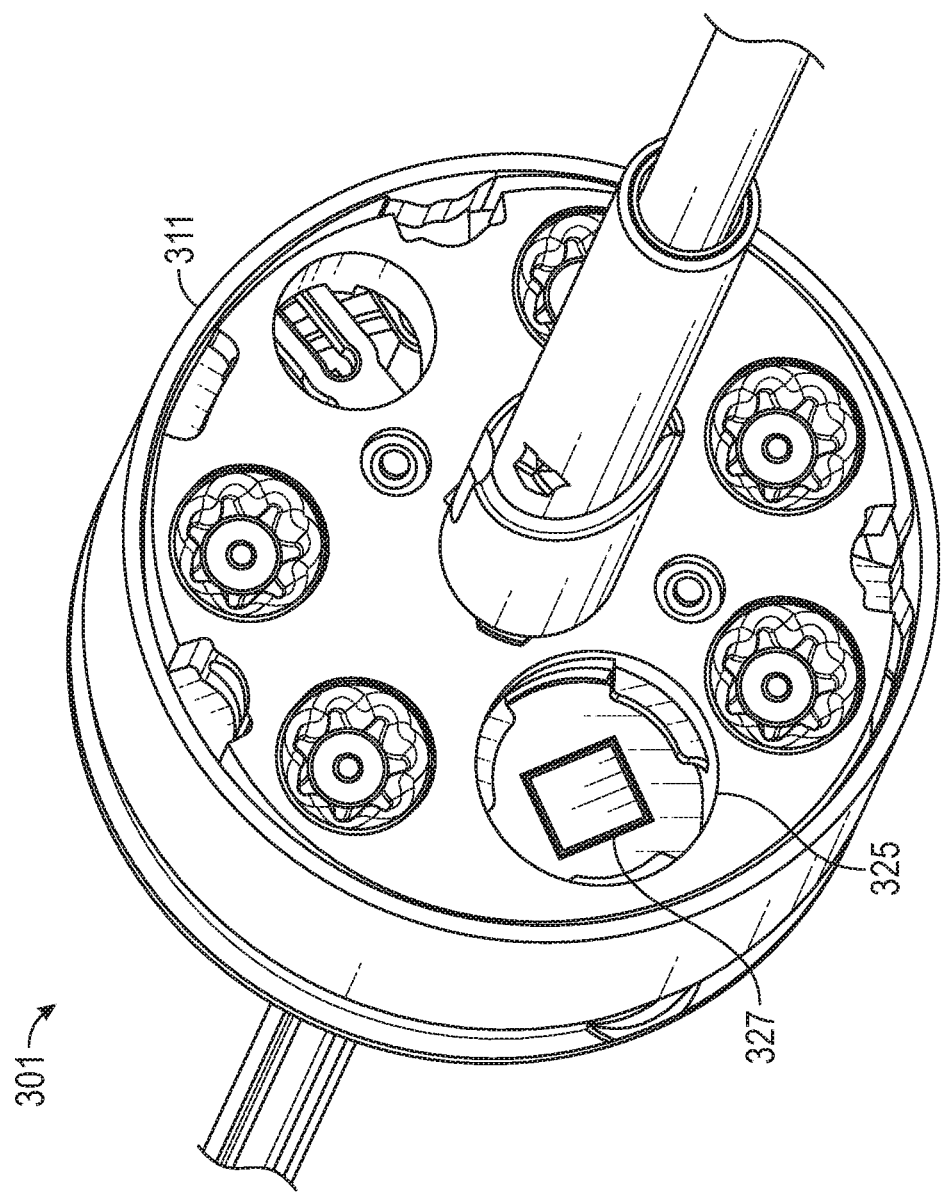
FIG. 26A illustrates another embodiment of a medical tool in accordance with aspects of this disclosure.
Figure 26B:
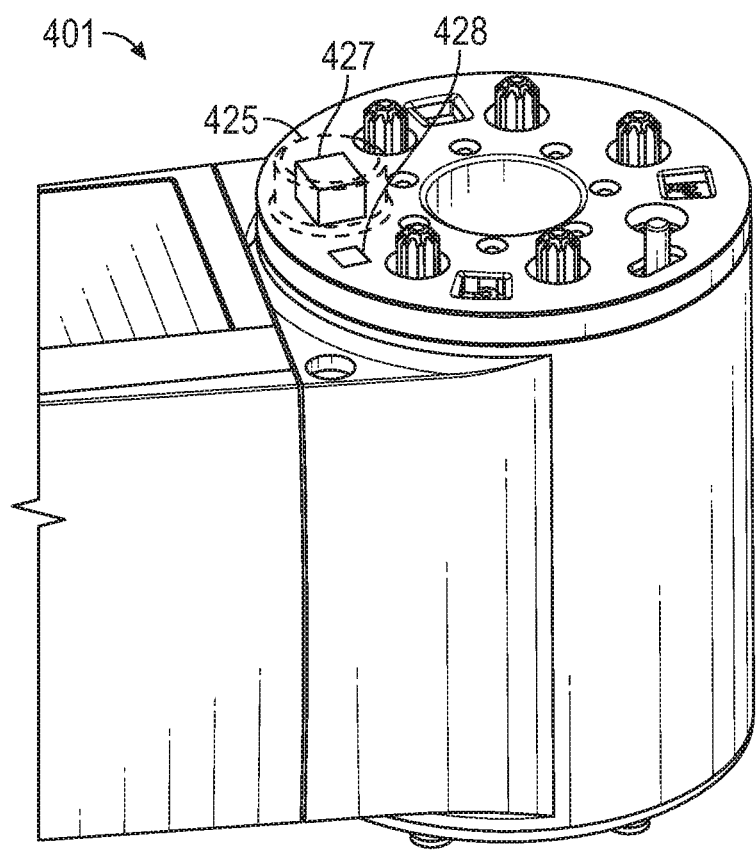
FIG. 26B illustrates another embodiment of a drive mechanism in accordance with aspects of this disclosure.
Figure 27:
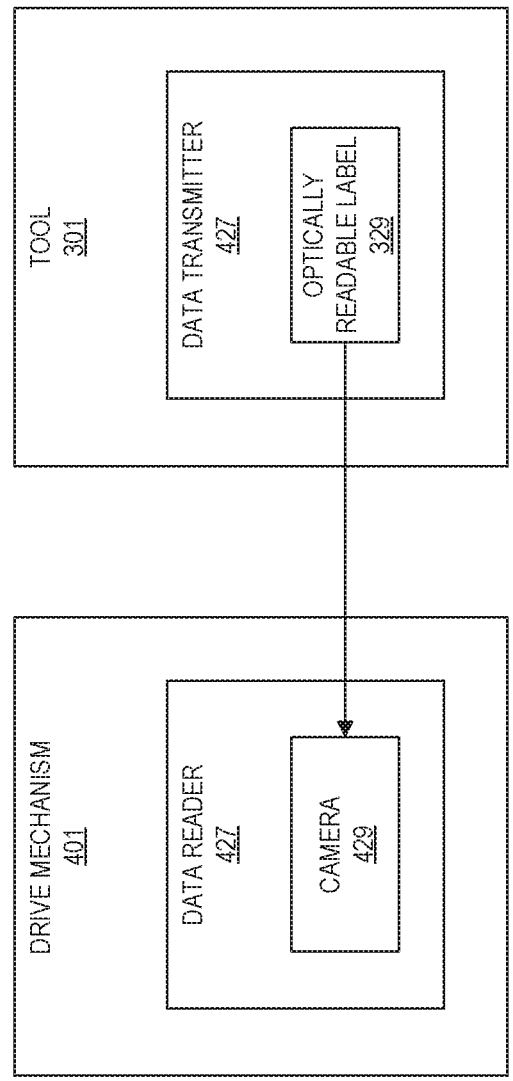
FIG. 27 is a schematic illustration of yet another embodiment of the medical tool and drive mechanism illustrated in FIGS. 26A-26B in accordance with aspects of this disclosure.

FIG. 26A illustrates another embodiment of a medical tool 301 in accordance with aspects of this disclosure. Certain aspects of the tool 301, including portions of the handle 311, may be similar to or the same as the components discussed above in connection with the tool 300 illustrated in FIG. 24. FIG. 26B illustrates another embodiment of a drive mechanism 401 in accordance with aspects of this disclosure. Certain aspects of the drive mechanism 401 may be similar to or the same as components discussed above in connection with the drive mechanism 400 and/or the adaptor 410 illustrated in FIG. 23A. In the FIG. 26B embodiment, the adaptor is not illustrated, showing corresponding portions of the drive mechanism that can be covered by the adaptor 410. FIG. 27 is a schematic illustration of yet another embodiment of the medical tool and drive mechanism illustrated in FIGS. 26A-26B in accordance with aspects of this disclosure.

As shown in FIGS. 26A-26B, tool 301 further includes a data transmitter 327 and the drive mechanism 401 further includes a data reader 427. The data transmitter 327 can be configured to transmit alignment data to the data reader 427 of the drive mechanism 401. Similarly, the data reader 427 can be configured to receive alignment data from the tool 401 (e.g., via the data transmitter 327) when the tool 401 is positioned within a threshold distance of the data reader 427.

A robotic system including the drive mechanism may be configured to solve the above described male/female spline 417/317 misalignment by using software calibration to align the angle of the output shafts 415 male splines 417 on the drive mechanism 401 to the angle of the input 315 female splines 317 on the tool 301 based on the alignment data transmitted from the tool 301 to the drive mechanism 401. By aligning the input 315 female splines 317 with the output shaft 415 male splines 417 prior to mechanically coupling the inputs 315 to the output shafts 415, the system may be able to provide a smooth loading experience, reducing any additional force and/or back driving required for alignment.

The mechanism for transmitting the alignment data from the tool 301 to the drive mechanism 401 may depend on the particular embodiment. For example, in some embodiments, the data reader 427 includes a wireless data receiver and the data transmitter 327 comprises a wireless data transmitter. The wireless data receiver can be configured to read the alignment data from the wireless data transmitter included on the tool 301.

In some embodiments, the wireless data transmitter comprises a radio frequency identification (RFID) reader and the wireless data transmitter comprises an RFID tag. The RFID reader can be configured to read the alignment data from the RFID tag. The RFID reader can be positioned within the reader housing 425 formed on the drive mechanism 401. The reader housing 425 can be formed of a different material (e.g., a plastic) from the rest of the face of the drive mechanism 401 and/or the adaptor 410, to thereby reduce the metal surfaces of the drive mechanism 401 from interfering with the RFID communication of the alignment data.

In some embodiments, the tool 301 may transmit the alignment data to the drive mechanism 401 over Bluetooth, and thus, the wireless data transmitter can include a Bluetooth reader and the wireless data transmitter can include a Bluetooth transmitter. As shown in FIG. 27, in other embodiments, the data reader 427 includes a camera 429 and the data transmitter 327 includes an optically readable label 329 visible on the tool 301. For example, the optically readable label 329 may be located within the recess 325 or any other surface of the tool 301 visible by the camera 429 when the tool 301 is being aligned with the drive mechanism 401. The camera 429 can be configured to read the alignment data from the optically readable label 329 visible on the tool. The camera 429 may also be located within the reader housing 425 or at another location on the drive mechanism (e.g., on the side of the drive mechanism 400 as shown in FIG. 21). In other embodiments, the locations of the camera and the optically readable label may be reversed, such that the camera is positioned on the tool 301 while the optically readable label is positioned on the drive mechanism 401.

A. Example Alignment Technique.

Figure 28:
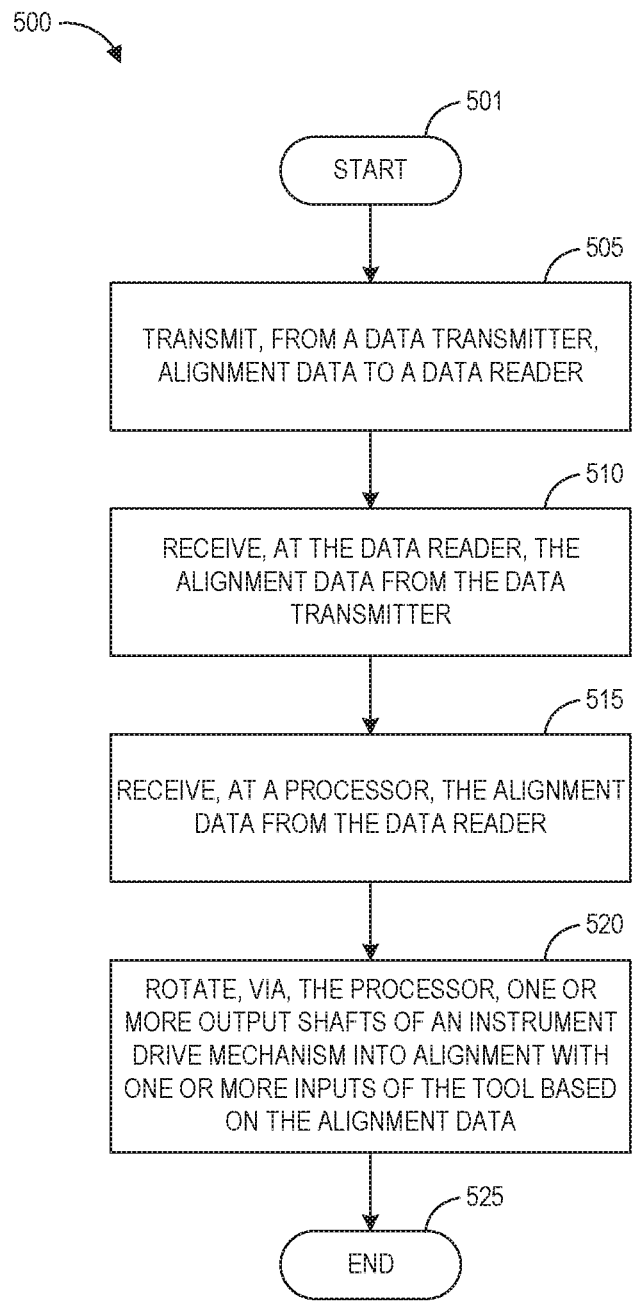
FIG. 28 is a flowchart illustrating an example method operable by a robotic system, or component(s) thereof, for alignment of tool inputs with drive mechanism output shafts in accordance with aspects of this disclosure.

FIG. 28 is a flowchart illustrating an example method 500 operable by a robotic system, or component(s) thereof, for alignment of tool inputs 315 with drive mechanism 401 output shafts 415 in accordance with aspects of this disclosure. For example, the steps of method 500 illustrated in FIG. 28 may be performed by processor(s) and/or other component(s) of a robotic system or associated system(s), including a data transmitter of a tool (e.g., the tool 301 of FIG. 26A) and a data receiver of a drive mechanism (e.g., the drive mechanism 401 of FIG. 27). For convenience, certain portions of the method 500 are described as performed by the robotic system, which is also referred to simply as the "system," in connection with the description of the method 500. The method 500 begins at block 501.

Figure 29:
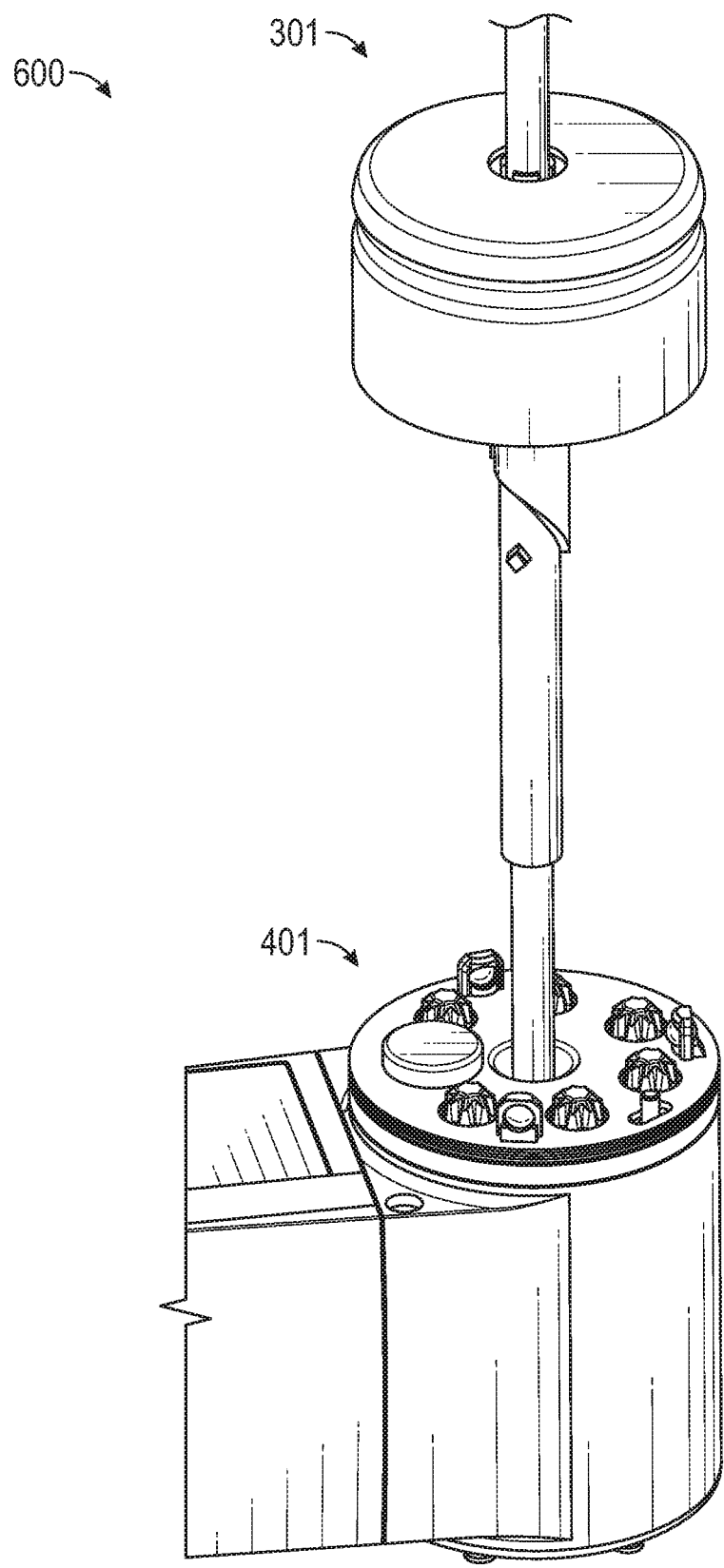
FIG. 29 illustrates a first stage during the alignment method of FIG. 28 in accordance with aspects of this disclosure.

FIG. 29 illustrates a first stage 600 during the alignment method 500 of FIG. 28 in accordance with aspects of this disclosure. In particular, the first stage 600 may occur prior to block 505 of the method 500, and may involve a user loading the tool 301 onto the drive mechanism 401. In some embodiments, loading may include moving the tool 301 from a first position to a second position, where in the second position the one or more inputs 315 of the tool are closer in distance to the one or more outputs 415 of the drive mechanism 401 than in the first position. Thus, the user can insert the shaft 330 of the tool 301 into the channel 430 formed in the drive mechanism. At the first stage 600, the male splines 417 on the output shafts 415 on the drive mechanism may not be aligned with the female splines 317 on the inputs 315 of the tool 301.

Referring to FIG. 28, at block 505, alignment data is transmitted from the data transmitter 327 to the data reader 427. In some embodiments, the transmitting of the alignment data of block 505 may occur during transition of the tool from the first position to the second position. The alignment data may be indicative of zero angles associated with each of the inputs 315 of the tool 301 when the pull wires of the tool 301 are unactuated. As used herein, the zero angle may define an angle or orientation of the female splines 317 of the inputs in the tool 301 to which the male splines 417 of the output shafts 415 of the drive mechanism 401 are to be aligned. Thus, the zero angle may define the angle of the inputs 315 of the tool 301 when no force is being applied externally to the inputs 315. When the output shafts 315 of the drive mechanism 401 are rotated to be in alignment with the zero angle, the drive mechanism 401 and tool 301 are capable of being coupled without requiring excessing force or back driving of the inputs 315.

In some embodiments, the zero angle can be established during manufacturing of the tool 301. In other embodiments, the zero angle can be adjusted after one or more uses of the tool 301 and drive mechanism 401, for example, when the tool 301 includes a data transmitter in the form of an RFID tag, the zero angle value stored in the RFID tag can be updated in response to changes in the length(s) of the pull wires after use of the tool 301. At the manufacturing stage, the zero angle for the tool 301 can be measured and stored in the data transmitter 327. For example, information regarding the zero angle can be loaded in an instrument specific configuration file on the instrument RFID tag when the data transmitter 327 is embodied as an RFID tag.

Figure 30:
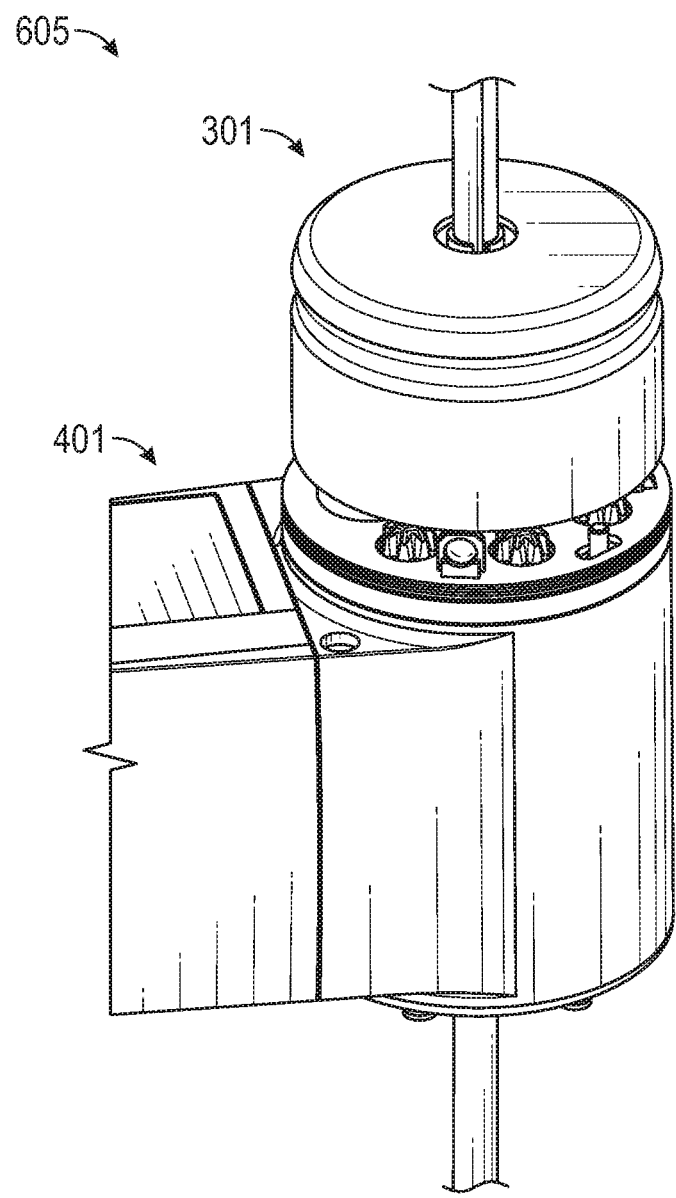
FIG. 30 illustrates a second stage during the alignment method of FIG. 28 in accordance with aspects of this disclosure.

At block 510, the method 500 involves receiving, at the data reader 427, the alignment data from the data transmitter 327. In some embodiments, the data reader 427 may only receive the alignment data when the data transmitter 327 is positioned within a threshold distance of the data reader 427. FIG. 30 illustrates a second stage 605 during the alignment method 500 of FIG. 28 in accordance with aspects of this disclosure. In particular, in the second stage 605, the tool 301 may be brought close enough to the drive mechanism 401 such that it is within the threshold distance of the data reader 427.

Since the drive mechanism may not include a processor, at block 515, the method 500 involves receiving, at a processor of the system, the alignment data from the data reader. At block 520, the method 500 involves rotating, via the processor, the one or more output shafts 415 of the drive mechanism 401 into alignment with the one or more inputs 315 of the tool 301 based on the alignment data.

Prior to rotating the output shafts 415, the processor may use the alignment information to determine whether the male splines 417 of the output shafts 415 are aligned with the female splines 317 of the inputs 315. At this point, if the processor detects misalignment, the processor may send a command to the drive mechanism to rotate the output splines of the output shafts 415 to match the angle of the female splines 317 of the inputs 315 on the tool 301. In the RFID embodiment, the RFID tag advantageously has a read distance that is greater than the distance at which the output shafts 415 contact with the inputs 315, thereby allowing the processor to adjust the output shafts 415 before contact with the inputs 315. In some embodiments, the drive mechanism 401 and/or the adaptor 410 can include an additional sensor (e.g., a Hall effect sensor 428) that can monitor the distance of the tool 301 RFID tag before using the RFID reader to read the RFID tag.

Figure 31:
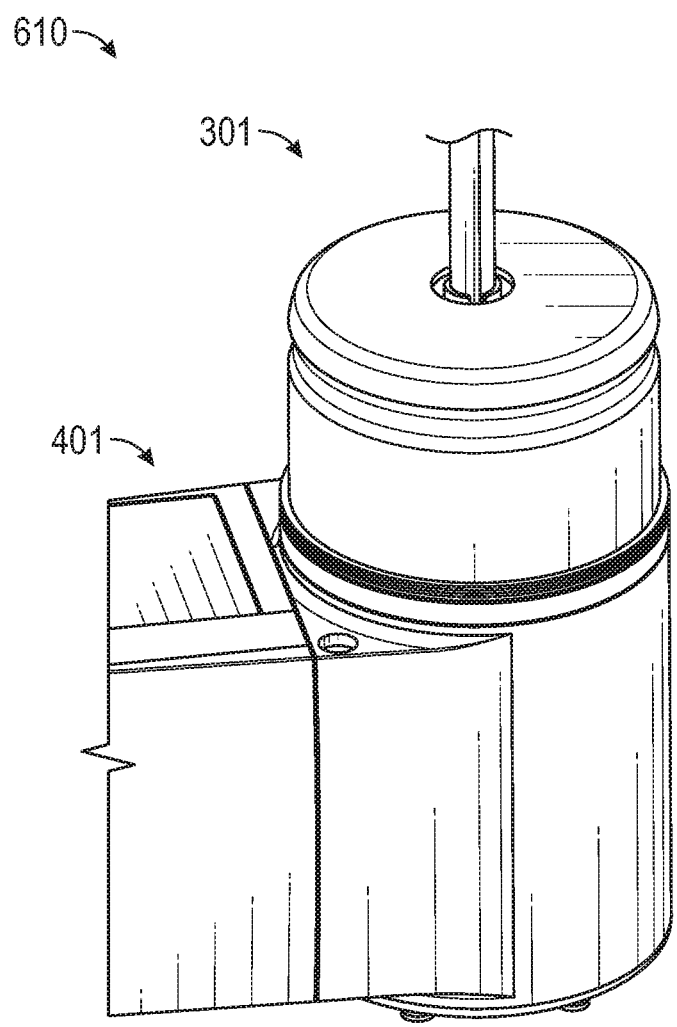
FIG. 31 illustrates a third stage during the alignment method of FIG. 28 in accordance with aspects of this disclosure.

The processor may be configured to rotate the output shafts 415 into alignment before the tool 301 is brought close enough for the inputs 315 to contact the output shafts 415. Thus, the output shafts 415 may be rotated into alignment with the inputs 315 such that the male splines 417 of the output shafts 415 can be engaged smoothly with the female splines 317 of the inputs 315 as the tool 301 is fully coupled to the drive mechanism 401. FIG. 31 illustrates a third stage 610 during the alignment method 500 of FIG. 28 in accordance with aspects of this disclosure. In particular, in the third stage 605 the tool 301 is coupled to the drive mechanism 401 after the output shafts 415 have been aligned with the inputs 315. The method 500 ends at block 525.

During usage of the tool 301 over time, the zero angle for the inputs 315 can change (e.g., the zero angle can drift due to changes in the lengths of the pull wires). In some embodiments, the system may be configured to load new values into the RFID tag so that the zero angles can be constantly updated. Thus, the processor can be configured to update the alignment data stored on the RFID tag in response to changes in the zero angles associated with each of the inputs 315 of the tool 301. As previously discussed, the zero angles can be indicative of the angles of the corresponding inputs 315 when the pull wires are unactuated.

Advantageously, by using pre-stored information in a data transmitter, the system can read the zero angle of the inputs 315 of the tool, enabling proper alignment angle between the inputs 315 and output shafts 415 without having to perform a more time consuming homing routine. In addition, by loading information into the data transmitter (e.g., at the manufacturing stage), the alignment can be performed by a software calibration process that can be easy to implement.

3. Implementing Systems and Terminology.

Implementations disclosed herein provide systems, methods and apparatus for aligning inputs of a medical instrument with output shafts of a drive mechanism.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The input/output shaft alignment functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic medical system, comprising:
    an instrument drive mechanism, comprising:
        one or more output shafts, each of the one or more output shafts configured to mechanically couple with a corresponding input of one or more inputs of a tool, wherein the tool comprises one or more pull wires configured to be actuated by the one or more output shafts via the one or more inputs;
        one or more motors respectively coupled to the one or more output shafts and configured to rotate the one or more output shafts; and
        a data reader configured to receive alignment data from the tool when the tool is positioned within a threshold distance of the data reader, the alignment data indicating an angle or orientation of a respective input when the one or more pull wires are unactuated; and
    at least one computer-readable memory in communication with at least one processor, the memory having stored thereon computer-executable instructions that cause the at least one processor to:
        receive the alignment data from the data reader; and
        adjust the one or more output shafts before contact with the one or more inputs, including rotating the one or more output shafts into alignment with the corresponding inputs of the tool based on the alignment data before the one or more output shafts make contact with the one or more inputs, the alignment data including the angle or orientation of the respective input when the one or more pull wires are unactuated.

2. The system of claim 1, wherein the data reader comprises a wireless data receiver configured to read the alignment data from a wireless data transmitter included on the tool.

3. The system of claim 2, wherein the wireless data receiver comprises a radio frequency identification (RFID) reader configured to read the alignment data from an RFID tag included on the tool.

4. The system of claim 3, wherein the instructions further cause the processor to update the alignment data stored on the RFID tag in response to changes in zero angles associated with each of the inputs of the tool, the zero angles being indicative of angles of the corresponding inputs when the pull wires are unactuated.

5. The system of claim 2, wherein the wireless data receiver comprises a Bluetooth reader configured to read the alignment data from a Bluetooth transmitter included on the tool.

6. The system of claim 1, wherein the data reader comprises a camera configured to read the alignment data from an optically readable label visible on the tool.

7. The system of claim 1, wherein each of the one or more output shafts comprises a male spline configured to couple with a female spline of the corresponding input of the tool.

8. The system of claim 1, wherein each of the output shafts is further configured to mechanically couple with the corresponding input of the tool via an adaptor.

9. The system of claim 1, wherein the data reader is further configured to receive the alignment data from the tool prior to the one or more output shafts being mechanically coupled with the one or more inputs of the tool.

10. The system of claim 1, wherein the alignment data is indicative of zero angles associated with each of the inputs of the tool when the pull wires are unactuated.

11. The system of claim 1, wherein the memory further includes instructions that cause the processor to:
    rotate the one or more output shafts to be in alignment with the angle or orientation of the corresponding input of the tool when the one or more pull wires are unactuated.

12. The system of claim 1, wherein:
the data reader is configured to receive the alignment data via one or more sensors of the tool when the tool is positioned within a threshold distance of the data reader; and
the instructions further cause the at least one processor to:
determine, from the alignment data, that the instrument drive mechanism is not rotationally aligned with the tool; and
in accordance with the determination, rotate the one or more output shafts into alignment with the corresponding input of the tool based on the alignment data such that a protrusion feature on the instrument drive mechanism enters an alignment groove of the tool.

13. A method of aligning an instrument drive mechanism with a tool, comprising:
receiving, at a data reader of the instrument drive mechanism, alignment data from the tool when the tool is positioned within a threshold distance of the data reader, wherein the tool comprises one or more inputs and one or more pull wires configured to be actuated by one or more output shafts of the instrument drive mechanism via the one or more inputs and the alignment data indicates an angle or orientation of a respective input when the one or more pull wires are unactuated;
receiving, at a processor, the alignment data from the data reader; and
adjusting, via the processor, the one or more output shafts before contact with the one or more inputs, including rotating the one or more output shafts of the instrument drive mechanism into alignment with the one or more inputs of the tool based on the alignment data before the one or more output shafts make contact with the one or more inputs, the alignment data including the angle or orientation of the respective input when the one or more pull wires are unactuated, wherein each of the one or more output shafts is configured to mechanically couple with a corresponding one of the inputs of the tool.

14. The method of claim 13, wherein the data reader comprises a wireless data receiver configured to read the alignment data from a wireless data transmitter included on the tool.

15. The method of claim 14, wherein the wireless data receiver comprises an RFID reader configured to read the alignment data from an RFID tag included on the tool.

16. The method of claim 15, further comprising:
updating the alignment data stored on the RFID tag in response to changes in zero angles associated with each of the inputs of the tool, the zero angles being indicative of angles of the corresponding inputs when the pull wires are unactuated.

17. The method of claim 13, wherein the data reader comprises a Bluetooth reader configured to read the alignment data from a Bluetooth transmitter included on the tool.

18. The method of claim 13, wherein each of the one or more output shafts comprises a male spline configured to couple with a female spline of the corresponding input of the tool.

19. The method of claim 13, further comprising:
mechanically coupling each of the output shafts with the corresponding input of the tool via an adaptor.

20. The method of claim 13, wherein the receiving of the alignment data from the tool is performed prior to the one or more output shafts being mechanically coupled with the one or more inputs of the tool.

21. The method of claim 13, wherein the alignment data is indicative of zero angles associated with each of the inputs of the tool when the pull wires are unactuated.

22. A non-transitory computer readable storage medium having stored thereon instructions that, when executed, cause at least one computing device to:
receive, at a data reader of an instrument drive mechanism, alignment data from a tool when the tool is positioned within a threshold distance of the data reader, wherein the tool comprises one or more inputs and one or more pull wires configured to be actuated by one or more output shafts of the instrument drive mechanism via the one or more inputs and the alignment data indicates an angle or orientation of a respective input when the one or more pull wires are unactuated;
receive, at the computing device, the alignment data from the data reader; and
adjust the one or more output shafts before contact with the one or more inputs, including rotating the one or more output shafts of the instrument drive mechanism into alignment with the one or more inputs of the tool based on the alignment data before the one or more output shafts make contact with the one or more inputs, the alignment data including the angle or orientation of the respective input when the one or more pull wires are unactuated,
wherein each of the output shafts is configured to mechanically couple with a corresponding one of the inputs of the tool.

23. The non-transitory computer readable storage medium of claim 22, wherein the data reader comprises a wireless data receiver configured to read the alignment data from a wireless data transmitter included on the tool.

24. The non-transitory computer readable storage medium of claim 23, wherein the wireless data receiver comprises an RFID reader configured to read the alignment data from an RFID tag included on the tool.

25. The non-transitory computer readable storage medium of claim 24, further having stored thereon instructions that, when executed, cause the at least one computing device to:
update the alignment data stored on the RFID tag in response to changes in zero angles associated with each of the inputs of the tool, the zero angles being indicative of angles of the corresponding inputs when the pull wires are unactuated.

26. The non-transitory computer readable storage medium of claim 22, wherein each of the one or more output shafts comprises a male spline configured to couple with a female spline of the corresponding input of the tool.

27. The non-transitory computer readable storage medium of claim 22, further having stored thereon instructions that, when executed, cause the at least one computing device to:
mechanically couple each of the output shafts with the corresponding input of the tool via an adaptor.

28. The non-transitory computer readable storage medium of claim 22, wherein the receiving of the alignment data from the tool is performed prior to the one or more output shafts being mechanically coupled with the one or more inputs of the tool.

29. The non-transitory computer readable storage medium of claim 22, wherein the alignment data is indicative of zero angles associated with each of the inputs of the tool when the pull wires are unactuated.

* * * * *